US012661389B2

(12) United States Patent
Yu et al.

(10) Patent No.: US 12,661,389 B2
(45) Date of Patent: *Jun. 23, 2026

(54) USE OF LOW pH ACTIVE ALPHA-1,4;/1,6-GLYCOSIDE HYDROLASES (GLCH) AS A FEED ADDITIVE FOR RUMINANTS TO ENHANCE STARCH DIGESTION

(71) Applicant: INTERNATIONAL N&H DENMARK APS, Kongens Lyngby (DK)

(72) Inventors: Shukun Yu, Malmo (SE); Karsten Matthias Kragh, Hoejbjerg (DK); Wenting Li, Wiltshire (GB)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/755,419

(22) Filed: Jun. 26, 2024

(65) Prior Publication Data

US 2024/0424068 A1      Dec. 26, 2024

Related U.S. Application Data

(63) Continuation of application No. 16/334,586, filed as application No. PCT/US2017/051758 on Sep. 15, 2017, now abandoned.

(60) Provisional application No. 62/398,741, filed on Sep. 23, 2016.

(51) Int. Cl.

| | |
|---|---|
| *A61K 38/47* | (2006.01) |
| *A23K 20/189* | (2016.01) |
| *A23K 50/10* | (2016.01) |
| *A61K 38/45* | (2006.01) |
| *A61K 38/48* | (2006.01) |
| *A61K 38/51* | (2006.01) |
| *A61K 38/52* | (2006.01) |
| *A61P 1/14* | (2006.01) |

(52) U.S. Cl.
CPC ............ *A61K 38/47* (2013.01); *A23K 20/189* (2016.05); *A23K 50/10* (2016.05); *A61K 38/45* (2013.01); *A61K 38/48* (2013.01); *A61K 38/51* (2013.01); *A61K 38/52* (2013.01); *A61P 1/14* (2018.01)

(58) Field of Classification Search
CPC ................................ A61K 38/47; A23K 50/10
See application file for complete search history.

(56) References Cited

U.S. PATENT DOCUMENTS

| | | |
|---|---|---|
| 5,231,017 A | 7/1993 | Lantero et al. |
| 6,352,851 B1 | 3/2002 | Nielsen et al. |
| 7,354,752 B2 | 4/2008 | Dunn-Coleman et al. |
| 7,413,879 B2 | 8/2008 | Dunn-Coleman et al. |
| 8,945,889 B2 | 2/2015 | Ge et al. |
| 2003/0165478 A1 | 9/2003 | Sokoll |
| 2005/0037053 A1 | 2/2005 | Isaksen et al. |
| 2006/0094080 A1 | 5/2006 | Dunn-Coleman et al. |
| 2015/0147786 A1 | 5/2015 | Clarkson et al. |
| 2015/0376668 A1 | 12/2015 | Ge et al. |
| 2021/0299229 A1 | 9/2021 | Yu et al. |

FOREIGN PATENT DOCUMENTS

| | | | | |
|---|---|---|---|---|
| BR | 0820483 A2 | 4/2022 | | |
| RU | 2129609 C1 | 4/1999 | | |
| RU | 2277345 C1 | 6/2006 | | |
| RU | 2529949 C2 | 10/2014 | | |
| WO | 8402921 A2 | 8/1984 | | |
| WO | 9200381 A1 | 1/1992 | | |
| WO | 0004136 A1 | 1/2000 | | |
| WO | 2003068256 A1 | 8/2003 | | |
| WO | 2005052148 A2 | 6/2005 | | |
| WO | 2005123911 A2 | 12/2005 | | |
| WO | 200806881 A1 | 1/2008 | | |
| WO | 2013110766 A1 | 8/2013 | | |
| WO | 2013169645 A1 | 11/2013 | | |
| WO | WO-2014020142 A1 * | 2/2014 | ............. | A23K 10/10 |
| WO | 2014099415 A1 | 6/2014 | | |
| WO | 2014099416 A1 | 6/2014 | | |
| WO | 2015128366 A2 | 9/2015 | | |

OTHER PUBLICATIONS

CAZy, "Glycoside Hydrolase Family 15"; Carbohydrate-Active Enzymes Database, https://www.cazy.org/GH15_characterized. html (accessed Jan. 2025)). (Year: 2025).*
Boel et al., "Glucoamylases G1 and G2 from Aspergillus niger are synthesized from two different but closely related mRNAs", The EMBO Journal, vol. 3, No. 5, 1984, pp. 1097-1102.
Chen et al., "Effect of replacing helical glycine residues with alanines on reversible and irreversible stability and production of Aspergillus awamori glucoamylase", Protein Engineering, vol. 9, No. 6, 1996, pp. 499-505.
Hata et al., "The Glucoamylase cDNA from Aspergillus oryzae: Its Cloning, Nucleotide Sequence, and Expression in *Saccharomyces cerevisiae*", Agric. Biol. Chem., 55 (4), 1991, pp. 941-949.
Fagerstrom et al., "Characterization, subsite mapping and partial amino acid sequence of glucoamylase from the filamentous fungus *Trichoderma reesei*", Biotechnology and Applied Biochemistry, vol. 21, Issue 2, pp. 223-231. (Year: 1995).
Swanson et al., "Kinetics of Maltose Hydrolysis by Glucoamylase", Biotechnology and Bioengineering, vol. 19, Issue 11, p. 1715-1718 (Year: 1977).

(Continued)

*Primary Examiner* — Melenie L Gordon
*Assistant Examiner* — Grant C Currens

(57)      ABSTRACT

Disclosed are uses of at least one alpha-1,4/1,6-glycoside hydrolase (GLCH) as a feed additive for a ruminant wherein said hydrolase: (a) has at least 20% activity at pH less than or equal to 3 in the presence of pepsin as compared to activity of the hydrolase at pH 6 in the presence of pepsin, (b) said hydrolase is active in at least two of three digestive chambers of a ruminant comprising a rumen, an abomasum and a small intestine and (c) the hydrolase works with pancreatic amylase to increase glucose yield.

9 Claims, 11 Drawing Sheets

(56)            References Cited

OTHER PUBLICATIONS

Westreicher-Kristen et al., "Postruminal digestion of starch infused into the abomasum of heifers with or without exogenous amylase administration", J. Anim. Sci. 2018.96:1939-1951.

Robbers, "Postruminal digestion of abomasally infused corn starch with or without exogenous amylase administration in cattle", Dissertation: Faculaty of Agricultural & Nutritional Sciences the Christian Albrechts University, Kiel, Germany, 2019, 118 pages. (English translation included).

Trotta et al., "Duodenal Infusions of Starch with Casein or Glutamic Acid Influence Pancreatic and Small Intestinal Carbohydrase Activities in Cattle", The Journal of Nutrition, vol. 150, Issue 4, Apr. 2020, pp. 784-791.

Remillard, "Starch digestion and digesta kinetics in the small intestine of steers fed on a maize grain and maize silage mixture", Animal Feed Science and Technology, vol. 30, Issues 1-2, Jul. 1990, pp. 79-89.

* cited by examiner

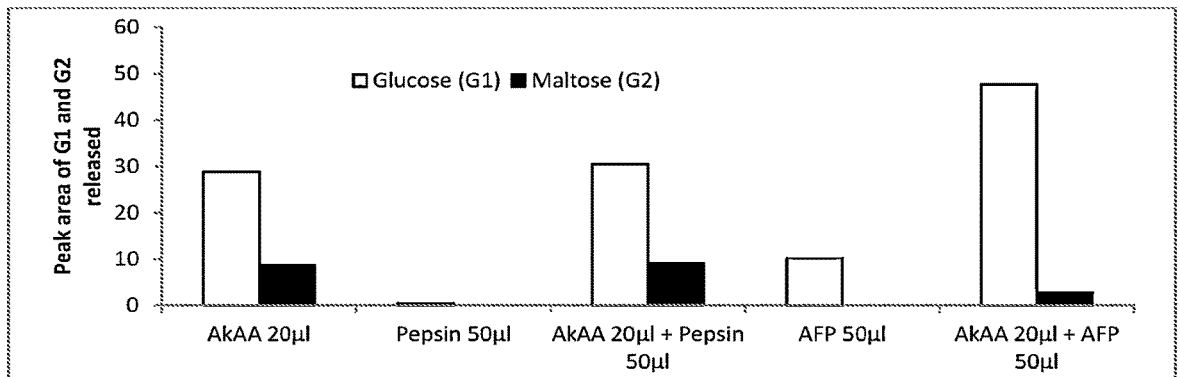
Figure 1. Release of glucose and maltose from corn flour by AkAA alpha-amylase in the presence of pepsin and AFP proteases at pH3.2.

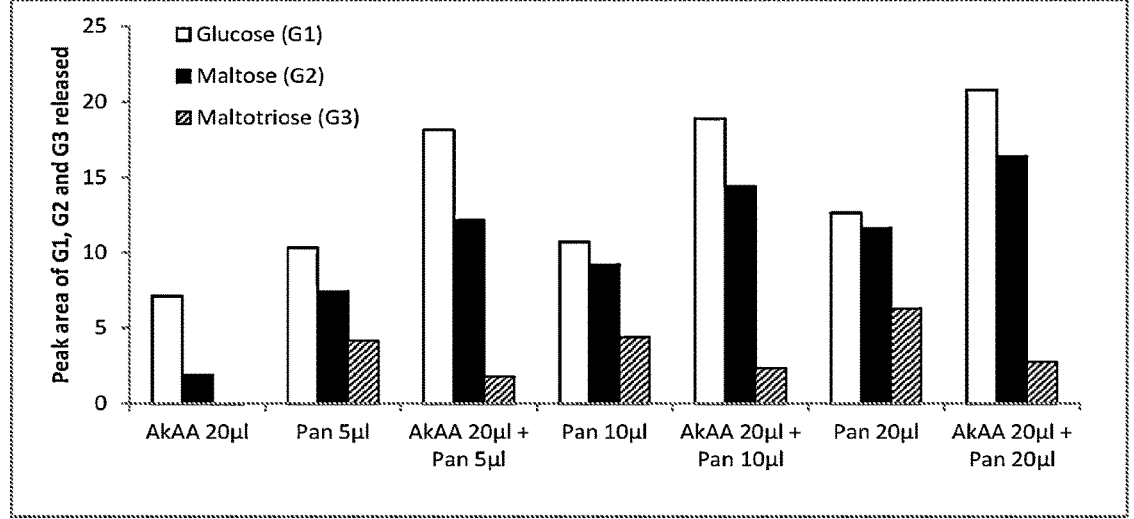
Figure 2. Release of glucose, maltose and maltotriose from corn flour by AkAA alpha-amylase and pancreatin at pH6.7 and the synergy of AkAA with pancreatin in increasing glucose and reducing maltotriose release.

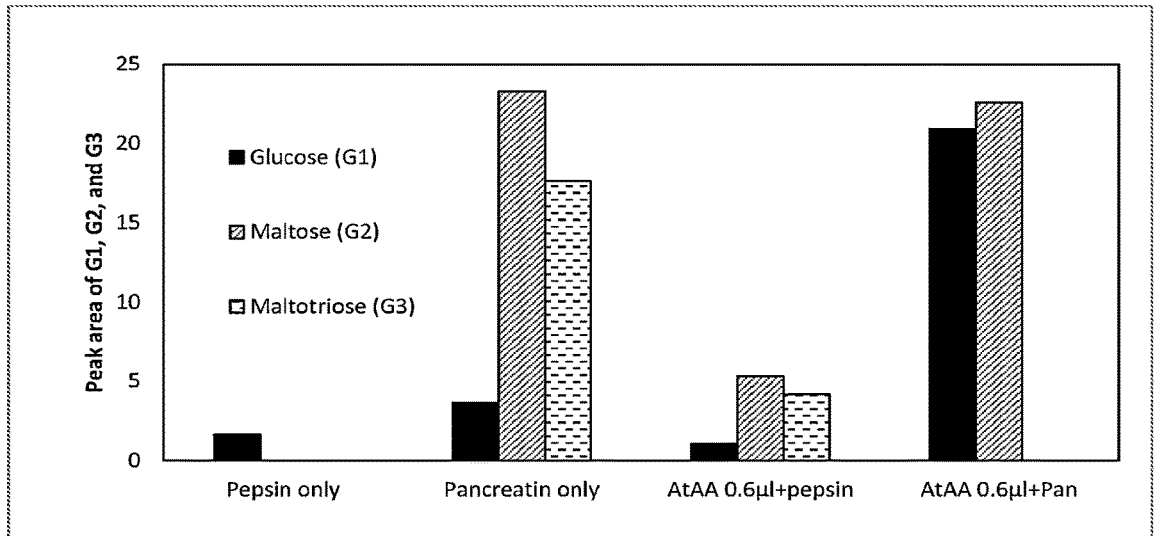
Figure 3. Activity of AtAA alpha-amylase on corn flour in the presence of pepsin at pH 2.5 and pancreatin at pH 6.7 and the complete conversion of maltotriose when AtAA and pancreatin were dosed together.

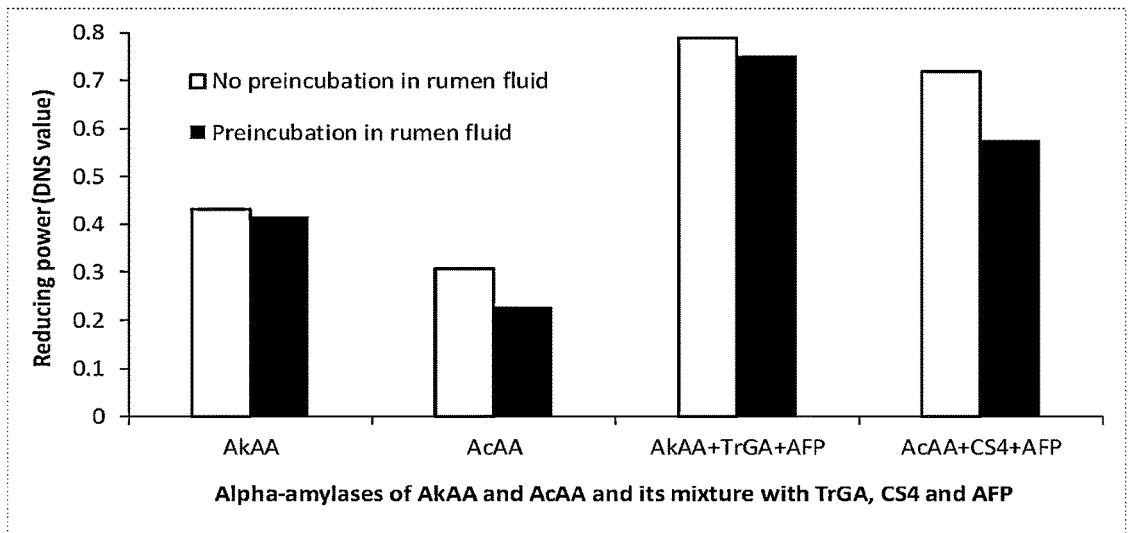
Figure 4. Stability of the alpha-amylases AkAA and AcAA and their mixture with a glucoamylase (TrGA or CS4) and an aspartic protease (AFP) when incubated with rumen fluid.

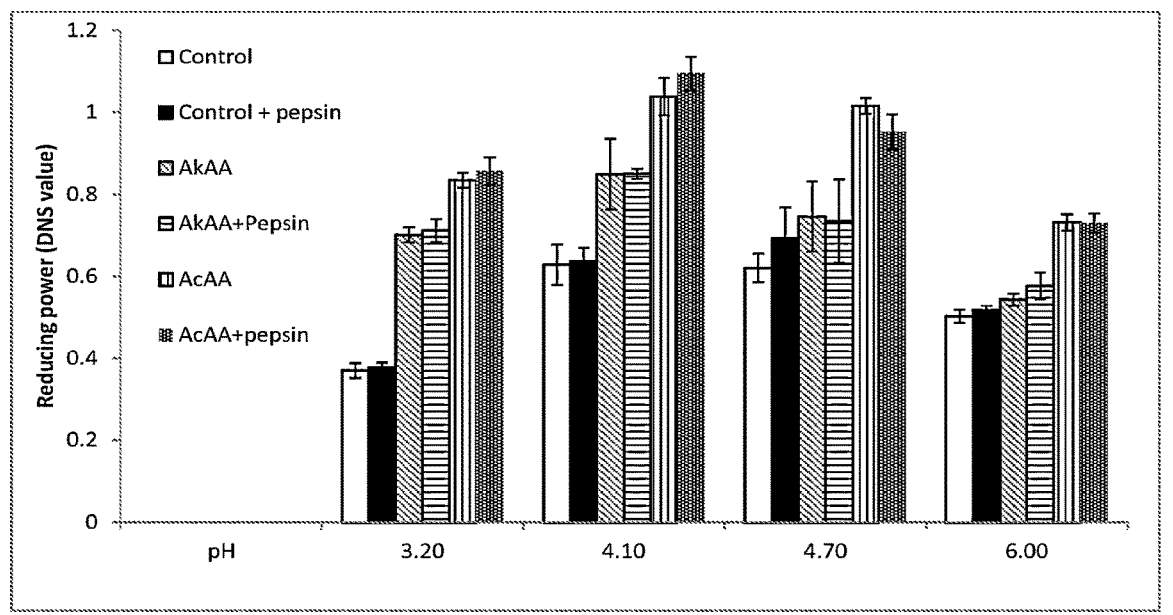
Figure 5. Activity of AkAA and AcAA alpha-amylases in the presence pepsin tested at pH 3.2-6.0.

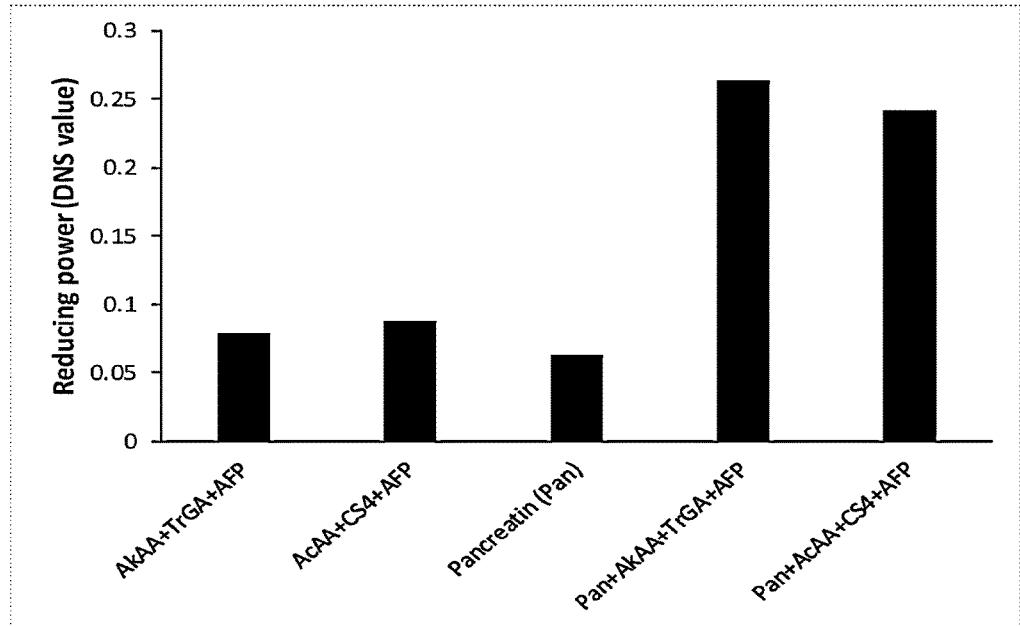
Figure 6. Activity of enzyme cocktails containing the alpha-amylases of AkAA or AcAA, and the glucoamylase (TrGA or CS4) and the aspartic peptidase (AFP) in the presence pancreatin (Pan) at pH6.0.

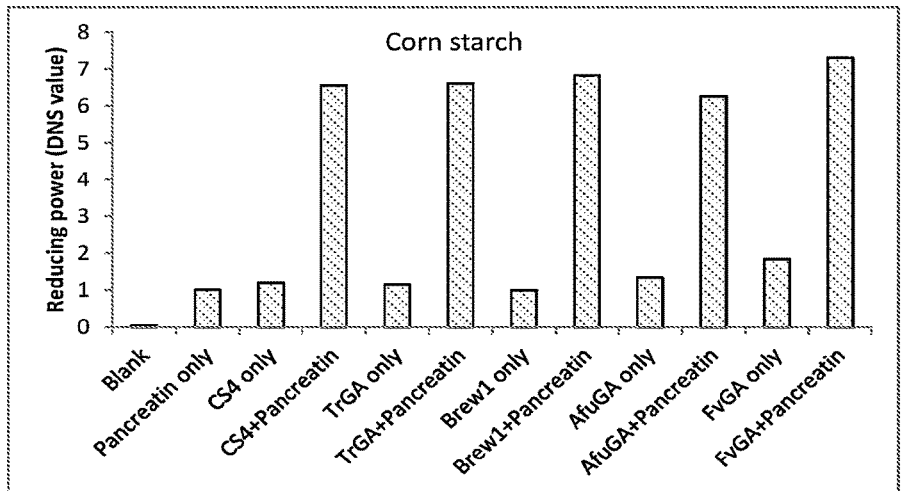
Figure 7. Interaction of glucoamylases CS4, TrGA, Brew1, AfuGA and FvGA with pancreatin at pH6.0 in increased hydrolysis of corn starch granules.

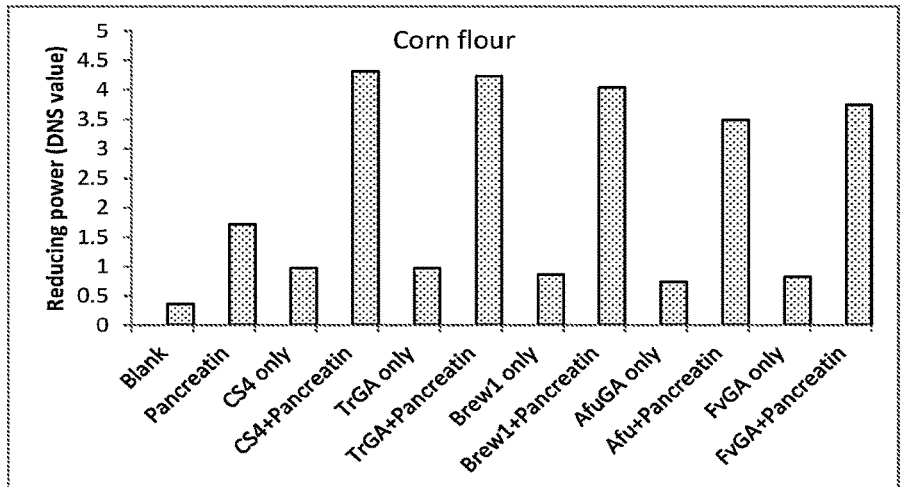
Figure 8. Interaction of glucoamylases CS4, TrGA, Brew1, AfuGA and FvGA with pancreatin at pH6.0 in increased hydrolysis of corn flour.

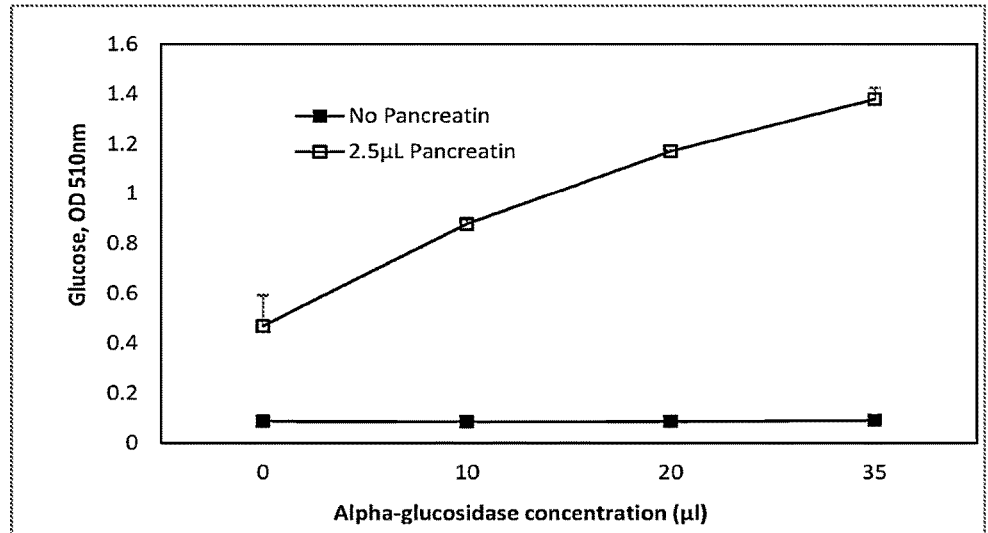
Figure 9. Release of glucose from corn starch granules by yeast maltase (alpha-glucosidase) in the presence of fixed amount of pancreatin at pH6.0.

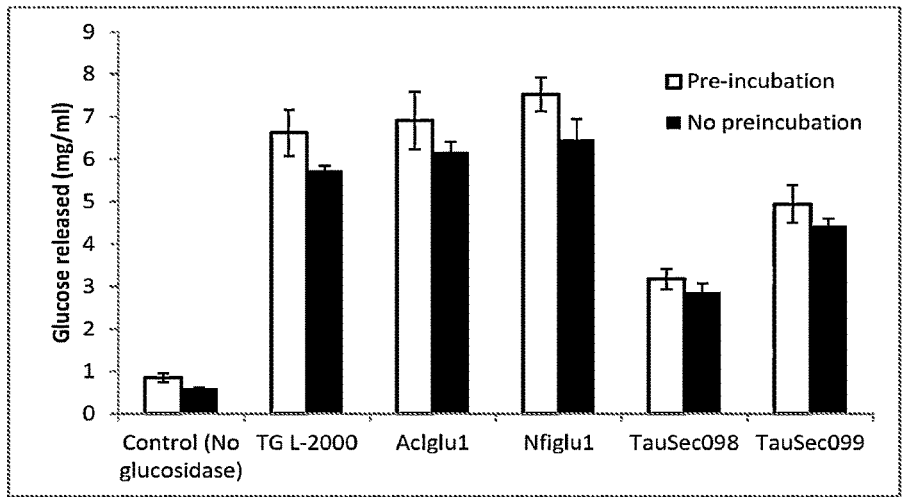
Figure 10. Stability of five alpha-glucosidases in ruminal fluid and interaction with pancreatin in release of glucose at pH6.0.

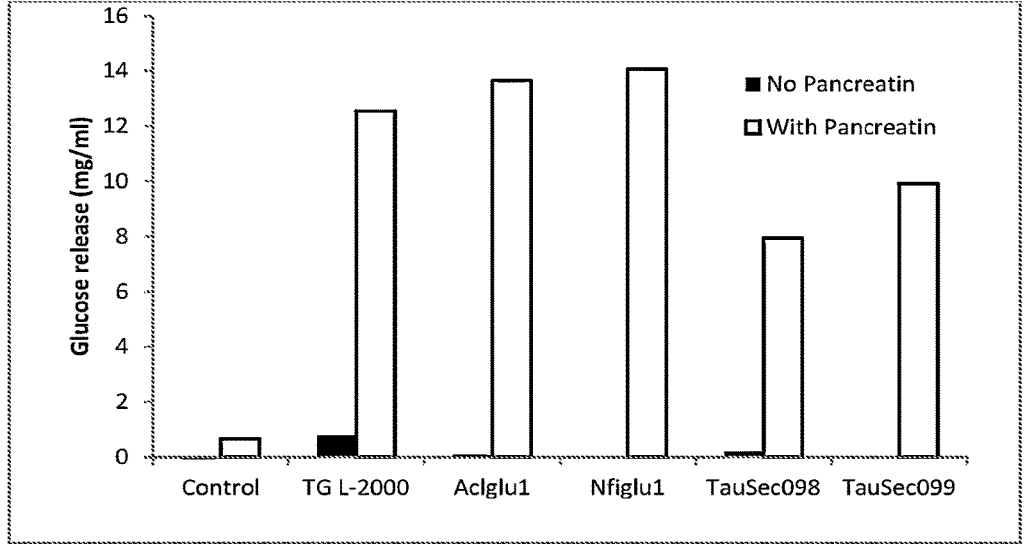
Figure 11. Release of glucose by five alpha-glucosidases incubated with pancreatin in at pH6.0.

USE OF LOW pH ACTIVE ALPHA-1,4;/1,6-GLYCOSIDE HYDROLASES (GLCH) AS A FEED ADDITIVE FOR RUMINANTS TO ENHANCE STARCH DIGESTION

FIELD

The field relates to animal nutrition and, in particular, to the use of low pH active alpha-1,4/1,6 glycoside hydrolases (GLCH) such as alpha-amylases, glucoamylases and alpha-glucosidases as a feed additive for ruminants to enhance starch digestion.

BACKGROUND

Ruminants have the unique ability to convert roughage into protein and energy through their microbial/enzyme digestive systems. Accordingly, ruminants play an important role in the earth's ecology and in the food chain.

The primary difference between ruminants and nonruminants is that ruminants' stomachs have four compartments: the rumen, reticulum, omasum, and abomasum. In the first two chambers, the rumen and the reticulum, the food is mixed with saliva and separates into layers of solid and liquid material. Solids clump together to form the cud or bolus.

The cud is then regurgitated and chewed to completely mix it with saliva and to break down the particle size. Fiber, especially cellulose and hemicellulose, is primarily broken down in these chambers by microbes (mostly bacteria, as well as some protozoa, fungi and yeast) into the three major volatile fatty acids (VFAs): acetic acid, propionic acid, and butyric acid. Protein and nonstructural carbohydrate (pectin, sugars, and starches) are also fermented.

Though the rumen and reticulum have different names, they represent the same functional space as digesta and can move back and forth between them. Together, these chambers are called the reticulorumen. The degraded digesta, which is now in the lower liquid part of the reticulorumen, then passes into the next chamber, the omasum, where water and many of the inorganic mineral elements are absorbed into the blood stream.

After this, the digesta is moved to the true stomach, the abomasum. The abomasum is the direct equivalent of the monogastric stomach, and digesta is digested here in much the same way. Digesta is finally moved into the small intestine, where the digestion and absorption of nutrients occurs. Microbes produced in the reticulorumen are also digested in the small intestine. Fermentation continues in the large intestine in the same way as in the reticulorumen.

Enzymes for use as feed additives ruminants are mainly fibrolytic enzymes, such as cellulases, beta-glucanases and hemicellulases (Table 1 in Beauchemin et al., 2004. A rationale for the development of feed enzyme products for ruminants. Can. J. Anim. Sci. 84:23-36). Reports on starch hydrolases for ruminant uses are limited. Starch hydrolases are grouped as endo- and exo-amylases.

Endoamylases, also called alpha-amylases (E.C. 3.2.1.1), are starch-degrading enzymes that catalyse the hydrolysis of internal alpha-1,4-O-glycosidic bonds in polysaccharides while retaining an alpha-anomeric configuration in the products. Most of the alpha-amylases need calcium ions ($Ca^{2+}$) for their activity, structural integrity and stability.

The alpha-amylase family, i.e., the clan GH-H of glycoside hydrolases is the largest family of glycoside hydrolases, transferases, and isomerases comprising nearly 30 different enzyme specificities. A large variety of enzymes are able to act on starch. These enzymes can be divided into four groups: endoamylases, exoamylases, debranching enzymes and transferases.

Endoamylases cleave internal alpha-1,4 bonds resulting in alpha-anomeric products.

Exoamylases cleave alpha-1,4 or alpha-1,6 bonds of the external glucose residues resulting in alpha- or beta-anomeric products.

Debranching enzymes hydrolyze alpha-1,6 bonds exclusively leaving long linear polysaccharides.

Transferases cleave alpha-1,4 glycosidic bond of the donor molecule and transfer part of the donor to a glycosidic acceptor forming a new glycosidic bond.

Glycoside hydrolases have been divided into classes based on their mode of reaction and families based on their well-defined amino acid sequence similarities. Most of the starch converting enzymes belong to GH-13 family. The GH-13 family can be further classified based on a larger unit called clan, which is the three-dimensional structure of catalytic module. Among the fourteen clans (A-N) defined for glycosidases and transglycosidases, alpha-amylase family (GH-13) belongs to the eighth clan GH-H.

Animals synthesize and secret digestive pancreatic alpha-amylase for starch hydrolysis. This alpha-amylase has an optimal pH around pH 6-7 and is active in the small intestine.

The addition of microbial amylases to feed can further increase animals' starch digestion possibly due to the fact that the secreted pancreatic amylase is not enough and/or the feed passage in the digestive tract of the small intestine is quite fast so that the pancreatic amylase does not have enough time to thoroughly digest the starch, especially in the case of poultry. (Isaksen, M. F. Cowieson, A. J. Kragh, K. M. (2010). Starch- and protein-degrading enzymes: biochemistry, enzymology and characteristics relevant to animal feed use. In: Enzymes in farm animal nutrition/edited by M. R. Bedford and G. G. Partridge. Pages 85-95).

Thus, endoamylases have been one of the feed enzymes widely used in the feed industry. The most common used feed amylases are derived from *Bacillus subtilis, B. amyloliquefaciens, B. licheniformis*, and *Aspergillus oryzae*.

These feed amylases have optimal activity in the pH range of pH4 to pH8. Most of them have considerable tolerance to pepsin. However, these feed enzymes appear not to have a raw starch binding domain (SBD) and may have limited capability to hydrolyze non-gelatinized raw starch.

Planchot et al., (Extensive degradation of native starch granules by alpha-amylase from *Aspergillus fumigalus*, Journal of Cereal Science, Volume 21, Issue 2, 1995, Pages 163-171), reported the low efficiency of alpha-amylase from *Bacillus* sp. in degrading granular starch compared to pancreatic amylase. EFSA (Scientific Opinion on the safety and efficacy of Ronozyme RumiStar (alpha-amylase) as a feed additive for dairy cows. Additives and Products or Substances used in Animal Feed (FEEDAP). EFSA Journal 2012; 10 (7): 2777) reported the use of an alpha-amylase from *B. licheniformis* for dairy cows. The effect was sometimes obvious and sometimes the effect was not significant. Dettori-Campus et al. (Hydrolysis of starch granules by the amylase from *Bacillus stearothermophilus* NCA 26. Process Biochemistry, Volume 27, Issue 1, January 1992, Pages 17-21) studied amylases from some 16 *Bacillus* strains and showed their preference for soluble starch instead of raw starch with the highest ratio of raw starch activity to soluble starch being 0.25 for *B. amylolyticus* strain.

Tricarico et al. (Dietary supplementation of ruminant diets with an *Aspergillus oryzae* alpha-amylase. Animal Feed Science and Technology. Volume 145, Issues 1-4, 14 Aug. 2008, Pages 136-150) reviewed the use of alpha-amylase from *Aspergillus oryzae* in dietary supplementation of ruminant diets and suggest that this amylase supplement may improve animal productivity by modifying ruminal starch digestion without necessarily increasing starch digestion in the rumen. Such effect could well come from enzyme impurities as by definition addition of amylase is expected to increase starch digestion (Beauchemin, Holtshausen, (2010). Developments in enzyme usage in ruminants. In: Developments in enzyme usage in ruminants. In: Enzymes in farm animal nutrition/edited by M. R. Bedford and G. G. Partridge. Pages 206-230).

Monteiro de Souza et al., (Application of microbial alpha-amylase in industry—a review. Brazilian Journal of Microbiology (2010) 41:850-861), reviewed alpha-amylases of industrial importance and almost all of them had a pH optimum above pH5 except for one from *Aspergillus kawachii* that had an optimal pH and stability at 3.0. It is the amylase *A. kawachii* that has been used together with glucoamylase for simultaneous liquefaction and fermentation of corn starch to bioethanol due to its capability to degrade raw starch or granular starch (Dunn-Coleman et al., 2008, U.S. Pat. No. 7,354,752 B2).

The digestibility of starch in feeds is highly variable and dependent on a number of factors including the physical structure of both the starch and feed matrix.

US Patent Application Publication 2005/0037053, published on Feb. 17, 2005, discloses the use of an enzyme having amylase activity and capable of degrading resistant starch in a feed comprising starch for monogastric animals such as poultry and swine.

WO 2008/06881, published on Jan. 17, 2008, discloses the use of bacterial amylases in feed for ruminant animals of the subfamily Bovinae for improving milk yield, apparent digestibility of the diet fed, feedstuff dry matter disappearance, weight gain and/or Feed Conversion Ratio.

WO 2015/128366, published on Sep. 3, 2015, discloses the use of bacterial amylases in combination with one or more proteases in feed for ruminant animals of the subfamily Bovinae for improving digestibility of maize and/or maize silages, in particular for improving milk yield, weight gain and/or Feed Conversion Ratio.

Accordingly, there is still a need to increase starch digestibility, increase glucose yield, increase digestion of dry matter and/or gas production for ruminants.

SUMMARY

In one embodiment, there is disclosed a method for increasing starch digestibility and glucose yield in a ruminant which comprises adding at least one alpha-1,4/1,6-glycoside hydrolase (GLCH) as a feed additive to feed for a ruminant wherein said hydrolase: (a) has at least 20% activity at pH less than or equal to 3 in the presence of pepsin as compared to activity of the hydrolase at pH 6 in the presence of pepsin, (b) said hydrolase is active in at least two of three digestive chambers of a ruminant comprising a rumen, an abomasum and a small intestine and (c) the hydrolase works with digestive enzymes present in the digestive chambers of the ruminant to increase starch digestibility and glucose yield.

In a second embodiment, the at least one GLCH enzyme is capable of hydrolyzing raw starch under conditions comparable to those found in the rumen or abomasum.

In a third embodiment, the hydrolase is selected from the group consisting of alpha-amylases, glucoamylases and alpha-glucosidases. Preferably, the group consists of alpha-amylases and glucoamylases.

In a fourth embodiment, the alpha-amylases are members of the GH 13 family or are selected from the group consisting of alpha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC3.2.1.60); iso-amylase (EC 3.2.1.68); glucodextranase (EC 3.2.1.70); maltohexaose-forming alpha-amylase (EC 3.2.1.98); maltotriose-forming alpha-amylase (EC 3.2.1.116); branching enzyme (EC 2.4.1.18); trehalose synthase (EC 5.4.99.16); 4-alpha-glucanotransferase (EC 2.4.1.25); maltopentaose-forming alpha-amylase (EC 3.2.1.-); amylo-sucrase (EC 2.4.1.4); sucrose phosphorylase (EC 2.4.1.7); malto-oligosyltrehalose trehalohydrolase (EC 3.2.1.141); isomaltulose synthase (EC 5.4.99.11); malto-oligosyltrehalose synthase (EC 5.4.99.15); amylo-alpha-1,6-glucosidase (EC 3.2.1.33); and alpha-1,4-glucan: phosphate alpha-maltosyltransferase (EC 2.4.99.16).

In a fifth embodiment, the glucosidases are members of the GH 13 or the GH31 family or are selected from the group consisting of alpha-glucosidase (EC 3.2.1.20); alpha-galactosidase (EC 3.2.1.22); alpha-mannosidase (EC 3.2.1.24); alpha-1,3-glucosidase (EC 3.2.1.84); sucrase-isomaltase (EC 3.2.1.48) (EC 3.2.1.10); alpha-xylosidase (EC 3.2.1.177); alpha-glucan lyase (EC 4.2.2.13); isomaltosyl-transferase (EC 2.4.1.-); oligosaccharide alpha-1,4-glucosyltransferase (EC 2.4.1.161); sulfoquinovosidase (EC 3.2.1.-).

In a sixth embodiment, the glucoamylases are members of the GH15 family or are selected from the group consisting glucoamylase (EC 3.2.1.3); glucodextranase. (EC 3.2.1.70); alpha-trehalase (EC 3.2.1.28); and dextran dextrinase (EC 2.4.1.2).

In a seventh embodiment, there is disclosed a method for increasing starch digestibility, increasing glucose yield, increase dry matter digestion and increase gas production during fermentation in a ruminant comprising adding to the feed an enzyme composition comprising (i) at least one GLCH enzyme as a feed additive for a ruminant wherein said enzyme: (a) has at least 20% activity at pH less than or equal to 3 in the presence of pepsin as compared to activity of the enzymes at pH 6 in the presence of pepsin, (b) said enzyme is active in at least two of three digestive chambers of a ruminant comprising a rumen, an abomasum and a small intestine and (c) the enzyme works with pancreatic amylase to increase glucose yield and (ii) at least one protease.

In a ninth embodiment, the at least one GLCH enzyme is capable of hydrolyzing raw starch.

In a tenth embodiment, the GLCH enzyme is selected from the group consisting of alpha-amylases, glucoamylases and alpha-glucosidases. Preferably, the enzyme is selected from the group consisting of alpha-amylases and glucoamylases.

In an eleventh embodiment, the at least one GLCH enzyme is selected from the group consisting alpha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC3.2.1.60); isoamylase (EC 3.2.1.68); glucodextranase (EC 3.2.1.70); maltohexaose-forming alpha-amylase (EC 3.2.1.98); maltotriose-forming alpha-amylase (EC 3.2.1.116); branching enzyme (EC 2.4.1.18); trehalose synthase (EC 5.4.99.16); 4-alpha-glucanotransferase (EC 2.4.1.25); maltopentaose-forming alpha-amylase (EC 3.2.1.-); amylosucrase (EC 2.4.1.4); sucrose phosphorylase (EC 2.4.1.7); malto-oligosyltrehalose trehalohydrolase (EC 3.2.1.141); isomaltulose synthase (EC 5.4.99.11); malto-oligosyltrehalose synthase (EC 5.4.99.15); amylo-alpha-1, 6-glucosidase (EC 3.2.1.33); and alpha-1,4-glucan: phosphate alpha-maltosyltransferase (EC 2.4.99.16).

In a twelfth embodiment, the glucosidases are selected from the group consisting of alpha-glucosidase (EC 3.2.1.20); alpha-galactosidase (EC 3.2.1.22); alpha-mannosidase (EC 3.2.1.24); alpha-1,3-glucosidase (EC 3.2.1.84); sucrase-isomaltase (EC 3.2.1.48) (EC 3.2.1.10); alpha-xylosidase (EC 3.2.1.177); alpha-glucan lyase (EC 4.2.2.13); isomaltosyltransferase (EC 2.4.1.-); oligosaccharide alpha-1,4-glucosyltransferase (EC 2.4.1.161); sulfoquinovosidase (EC 3.2.1.-).

In the thirteenth embodiment, the glucoamylases are selected from the GH15 glycosyl hydrolase family.

In a fourteenth embodiment, the protease is selected from the group consisting of an acid protease or a neutral metalloprotease and, preferably, the protease is a fungal aspartic protease or a bacterial neutral metalloprotease.

BRIEF DESCRIPTION OF THE FIGURES

FIG. 1 depicts the release of glucose and maltose from corn flour by AkAA alpha-amylase in the presence of pepsin and AFP protease (Example 2).

FIG. 2 depicts the release of glucose maltose and maltotriose from corn flour by AkAA alpha-amylase and pancreatin and the synergy of AkAA with pancreatin in increasing glucose and reducing maltotriose release (Example 4).

FIG. 3 shows the activity of AtAA alpha-amylase on corn flour in the presence of pepsin at pH 2.5 and pancreatin at pH 6.7 and the complete conversion of maltotriose when AtAA and pancreatin were dosed together (Example 5).

FIG. 4 shows the stability of the alpha-amylases AkAA and AcAA and their mixture with glucoamylases TrGA and CS4 and aspartyl protease when incubated with rumen fluid (Example 6).

FIG. 5 shows the activity of AkAA and AcAA alpha-amylases in the presence pepsin tested at pH 3.2-6.0 (Example 7).

FIG. 6 shows the activity of the enzyme cocktails containing alpha-amylases AkAA, AcAA, and glucoamylase TrGA, CS4, and the aspartyl peptidase AFP in the presence pancreatin (Example 8).

FIG. 7 shows glucoamylase interaction with pancreatin in increased hydrolysis of corn starch granules (Example 10).

FIG. 8 shows glucoamylase interaction with pancreatin in increased hydrolysis of corn flour (Example 10).

FIG. 9 shows the release of glucose from corn starch granules by yeast maltase (alpha-glucosidase) in the presence of fixed amount of pancreatin (Example 13).

FIG. 10 shows the stability of five alpha-glucosidases in ruminal fluid and interaction with pancreatin in the release of glucose (Example 15).

FIG. 11 shows the interaction of the five alpha-glucosidases with pancreatin in the release of glucose at pH6.0 (Example 16).

6

DETAILED DESCRIPTION

All patents, patent applications, and publications cited are incorporated herein by reference in their entirety.

In this disclosure, a number of terms and abbreviations are used. The following definitions apply unless specifically stated otherwise.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

The terms alpha-1,4/1,6-glycoside hydrolases or alpha-1, 4; 1,6-glycoside hydrolases are used interchangeably herein ("GLCH"). They refer to enzymes capable of hydrolyzing alpha-1,4 linkages and/or alpha-1,6 linkages in an oligomer or polymer molecules wherein these glycoside hydrolases that (a) have at least 20% activity at pH less than or equal to 3 in the presence of pepsin as compared to activity of the enzymes at pH 6 in the presence of pepsin, (b) such enzymes are active in at least two of three digestive chambers of a ruminant comprising a rumen, an abomasum and a small intestine and (c) the enzymes work with pancreatic amylase to increase glucose yield. Preferably, these enzymes have one or two carbohydrate binding modules and are capable of hydrolyzing raw starch. Preferably, these glycoside hydrolase enzymes are selected from the group consisting of alpha-amylases, glucoamylases and/or alpha-glucosidases.

The term "glycoside hydrolase" is used interchangeably with "glycosidases" and "glycosyl hydrolases". Glycoside hydrolases assist in the hydrolysis of glycosidic bonds in complex sugars (polysaccharides). Together with glycosyltransferases, glycosidases form the major catalytic machinery for the synthesis and breakage of glycosidic bonds. Glycoside hydrolases are classified into EC 3.2.1 as enzymes catalyzing the hydrolysis of O- or S-glycosides. Glycoside hydrolases can also be classified according to the stereochemical outcome of the hydrolysis reaction. Thus, they can be classified as either retaining or inverting enzymes. Glycoside hydrolases can also be classified as exo- or endo-acting, dependent upon whether they act at the (usually non-reducing) end or in the middle, respectively, of an oligo/polysaccharide chain. Glycoside hydrolases may also be classified by sequence or structure based methods. They are typically named after the substrate that they act upon.

The term "glycosyltransferase" refers to an enzyme that catalyzes the formation of a glycosidic bond between monosaccharides.

The terms "glycan" and "polysaccharide" are used interchangeably herein. Glycan refers to a polysaccharide or oligosaccharide, or the carbohydrate section of a glycoconjugate such as a glycoprotein, a glycolipid, or a proteoglycan, even if the carbohydrate is only an oligosaccharide. Glycans may be homo- or heteropolymers of monosaccharide residues. They may be linear or branched molecules. Glycans can be found attached to proteins as in glycoproteins and proteoglycans. In general, they are found on the exterior surface of cells. O- and N-linked glycans are very common in eukaryotes but may also be found, although less commonly, in prokaryotes.

The term "alpha-amylase" is used interchangeably with alpha-1,4-D-glucan glucanohydrolase and glycogenase. Alpha-amylases (E.C. 3.2.1.1) usually, but not always, need calcium in order to function. These enzymes catalyze the endohydrolysis of alpha-1,4-glucosidic linkages in oligosaccharides and polysaccharides. Alpha-amylases act on, starch, glycogen, and related polysaccharides and oligosaccharides in a random manner, liberating reducing groups in the alpha-configuration.

The term "low pH active alphaamylase ("LpHAA") refers to an alpha-amylase that that has at least 20% activity at pH less than or equal to 3.0 compared its activity at pH 6.0. The term "glucoamylase" (EC 3.2.1.3) is used interchangeably with glucan 1,4-alpha-glucosidase, amyloglucosidase, gamma-amylase, lysosomal alpha-glucosidase, acid maltase, exo-1,4-alpha-glucosidase, glucose amylase, gamma-1,4-glucan glucohydrolase, acid maltase, and 1,4-alpha-D-glucan hydrolase. This enzyme cleaves the last alpha-1,4-glycosidic linkages at the non-reducing end of amylose and amylopectin to yield glucose. It also cleaves the alpha-1,6-glycosidic linkages.

The term "alpha-glucosidase" (E.C.3.2.1.20) is used interchangeably with maltase, glucoinvertase, glucosiosucrase, maltase-glucoamylase, alpha-glucopyranosidase, glucosido-invertase, alpha-D-glucosidase, alpha-glucoside hydrolase, alpha-1,4-glucosidase, and alpha-D-glucoside glucohydrolase. This enzyme hydrolyzes terminal non-reducing (1-4) linked alpha-glucose residues to release a single alpha-glucose molecule. Alpha-glucosidase is a carbohydrate-hydrolase that releases alpha-glucose as opposed to beta-glucose.

The term "feed" is used with reference to products that are fed to animals in the rearing of livestock. The terms "feed" and "animal feed" are used interchangeably. In a preferred embodiment, the food or feed is for consumption by non-ruminants and ruminants.

The term "direct fed microbial" ("DFM") as used herein is source of live (viable) naturally occurring microorganisms. Categories of DFMs include *Bacillus*, Lactic Acid Bacteria and Yeasts. *Bacillus* are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets. Types of Lactic Acid Bacteria include *Bifidobacterium, Lactobacillus* and *Streptococcus*. Yeasts are not bacteria. These microorganisms belong to the plant group fungi.

The term "protease" as used herein refers to an enzyme capable of cleaving a peptide bond. The terms "protease", "peptidase" and "proteinase" can be used interchangeably. Proteases can be found in animals, plants, bacteria, archaea and viruses. Proteolysis can be achieved by enzymes currently classified into six broad groups: aspartic proteases, cysteine proteases, serine proteases, threonine proteases, glutamic proteases, and metalloproteases.

In particular, the term "protease" means a protein or polypeptide domain of derived from a microorganism, e.g., a fungus, bacterium, or from a plant or animal, and that has the ability to catalyze cleavage of peptide bonds at one or more of various positions of a protein backbone (e.g., E.C. 3.4).

The term "acid protease" means a protease having the ability to hydrolyze proteins under acidic conditions. It can encompass any number of protein-hydrolyzing agents such as endopeptidases or exopeptidases.

The terms "aspartic protease" and "aspartic acid protease" are used interchangeably herein and are a type of acid protease. Aspartic proteases (EC 3.4.23), also known as aspartyl proteases, an activated water molecule bound to one or more catalytic aspartate residues to hydrolyze a peptide bond in a polypeptide substrate. Generally, they have two highly conserved aspartates in the active site and are optimally active at acidic pH.

The abbreviation "AFP" refers to an aspartic fungal protease, that is, an aspartic protease from a fungal organism source.

The term "metalloprotease" is any protease whose catalytic mechanism involves a metal. Most metalloproteases require zinc, but some use cobalt. The metal ion is coordinated to the protein via three ligands. The ligands coordinating the metal ion can vary with histidine, glutamate, aspartate, lysine, and arginine. The fourth coordination position is taken up by a labile water molecule.

There are two subgroups of metalloproteinases include (a) exopeptidases, metalloexopeptidases (EC number: 3.4.17), and (b), metalloendopeptidases (3.4.24). Well known metalloendopeptidases include ADAM proteins and matrix metalloproteinases.

The term "pepsin" as used herein refers to an enzyme that breaks down proteins into smaller peptides at a low pH from 2.0 to 3.5, i.e., it is a protease belonging to Aspartic peptidase family A1. It is produced and secreted into the stomach and is one of the main digestive enzymes in the digestive systems of humans and animals, where it helps digesting the proteins in food or feed.

The term "ruminant" as used herein refers to a mammal that is able to acquire nutrients from plant-based food by fermenting it in a specialized stomach prior to digestion, principally, through microbial actions. The process typically requires the fermented ingesta (known as cud) to be regurgitated and chewed again. The process of rechewing the cud to further break down plant matter and stimulate digestion is called rumination. Roughly 150 species of ruminants include both domestic and wild species. Ruminating animals include, but are not limited to, cattle, cows, goats, sheep, giraffes, yaks, deer, elk, antelope, buffalo and the like.

The term "digestive chambers of a ruminant" as used herein refer to the rumen, reticulum, omasum, abomasum and small intestine (McDonald et al., 2011, Animal Nutrition (7th Edition), pages 156-191). The abomasum is the direct equivalent of the monogastric stomach.

The term "fodder" as used herein refers to a type of animal feed, is any agricultural foodstuff used specifically to feed domesticated livestock, such as cattle, goats, sheep, horses, chickens and pigs. "Fodder" refers particularly to food given to the animals (including plants cut and carried to them), rather than that which they forage for themselves (called forage). Fodder is also called provender and includes hay, straw, silage, compressed and pelleted feeds, oils and mixed rations, and sprouted grains and legumes (such as bean sprouts, fresh malt, or spent malt). Most animal feed is from plants, but some manufacturers add ingredients to processed feeds that are of animal origin.

The term "feed" is used with reference to products that are fed to animals in the rearing of livestock. The terms "feed" and "animal feed" are used interchangeably.

The term "starch" is used interchangeably with "amylum". It is a polymeric carbohydrate consisting of a large number of glucose units joined by glycosidic bonds and is the most common storage carbohydrate in plants. Thus, "starch" can refer to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

The terms "starch binding domain (SBD) or carbohydrate binding module (CBM)" are used interchangeably herein. SBDs can be divided into nine CBM families. As a source of energy, starch is degraded by a large number of various amylolytic enzymes. However, only about 10% of them are capable of binding and degrading raw starch. These enzymes usually possess a distinct sequence-structural module called the starch-binding domain that mediates attachment to starch granules. SBD refers to an amino acid sequence that binds preferentially to a starch (polysaccharide) substrate or a maltosaccharide, alpha-, beta and gamma-cyclodextrin and the like. They are usually motifs of approximately 100 amino acid residues found in about 10% of microbial amylolytic enzymes.

The term "catalytic domain" refers to a structural region of a polypeptide which is distinct from the CBM and which contains the active site for substrate hydrolysis.

The term "granular starch" refers to raw (uncooked) starch, e.g., granular starch that has not been subject to gelatinization.

The terms "granular starch hydrolyzing (GSH) enzyme" and "granular starch hydrolyzing (GSH) activity" are used interchangeably herein and refer to enzymes, which have the ability to hydrolyze starch in granular form under digestive tract relevant conditions comparable to the conditions found in the digestive tract of animals and, in particular, ruminants.

The term "gelatinization" refers to breaking down the intermolecular bonds of starch molecules in the presence of water and heat, allowing the hydrogen bonding sites to engage more water. This irreversibly dissolves the starch granule in water to form a viscous suspension.

The term "degree of polymerization (DP)" refers to the number of monomeric units in a macromolecule or polymer or oligomer molecule. For example, it can refer to the number (n) of monomer units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

The terms "peptides", "proteins" and "polypeptides are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine(S) is represented as "G087S" or "G87S". When describing modifications, a position followed by amino acids listed in parentheses indicates a list of substitutions at that position by any of the listed amino acids. For example, 6 (L, I) means position 6 can be substituted with a leucine or isoleucine. At times, in a sequence, a slash (/) is used to define substitutions, e.g. F/V, indicates that the particular position may have a phenylalanine or valine at that position.

Mutations can be named by the one letter code for the parent amino acid, followed by a position number and then the one letter code for the variant amino acid. For example, mutating glycine (G) at position 87 to serine(S) is represented as "G087S" or "G87S".

The term "mature" form of a protein, polypeptide, or peptide refers to the functional form of the protein, polypeptide, or enzyme without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

A "prosequence" or "propeptide sequence" refers to an amino acid sequence between the signal peptide sequence and mature enzyme sequence (e.g., a glycoside hydrolase as described herein) that is necessary for the proper folding and secretion of an enzyme; they are sometimes referred to as intramolecular chaperones. Cleavage of the prosequence or propeptide sequence results in a mature active enzyme which are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported. The gene of interest may be expressed with or without a signal sequence.

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "amino acid" refers to the basic chemical structural unit of a protein or polypeptide. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

The term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

The term "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "coding sequence" refers to a nucleotide sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The terms "regulatory sequence" or "control sequence" are used interchangeably herein and refer to a segment of a nucleotide sequence which is capable of increasing or decreasing expression of specific genes within an organism. Examples of regulatory sequences include, but are not limited to, promoters, signal sequence, operators and the like. As noted above, regulatory sequences can be operably linked in sense or antisense orientation to the coding sequence/gene of interest.

"Promoter" or "promoter sequences" refer to DNA sequences that define where transcription of a gene by RNA polymerase begins. Promoter sequences are typically located directly upstream or at the 5' end of the transcription initiation site. Promoters may be derived in their entirety from a native or naturally occurring sequence, or be composed of different elements derived from different promoters found in nature, or even comprise synthetic DNA segments. It is understood by those skilled in the art that different promoters may direct the expression of a gene in different tissues or cell type or at different stages of development, or in response to different environmental or physiological conditions ("inducible promoters").

The "3' non-coding sequences" refer to DNA sequences located downstream of a coding sequence and include sequences encoding regulatory signals capable of affecting mRNA processing or gene expression, such as termination of transcription.

The term "transformation" as used herein refers to the transfer or introduction of a nucleic acid molecule into a host organism. The nucleic acid molecule may be introduced as a linear or circular form of DNA. The nucleic acid molecule may be a plasmid that replicates autonomously, or it may integrate into the genome of a production host. Production hosts containing the transformed nucleic acid are referred to as "transformed" or "recombinant" or "transgenic" organisms or "transformants".

The term "recombinant" as used herein refers to an artificial combination of two otherwise separated segments of nucleic acid sequences, e.g., by chemical synthesis or by the manipulation of isolated segments of nucleic acids by genetic engineering techniques. For example, DNA in which one or more segments or genes have been inserted, either naturally or by laboratory manipulation, from a different molecule, from another part of the same molecule, or an artificial sequence, resulting in the introduction of a new sequence in a gene and subsequently in an organism. The terms "recombinant", "transgenic", "transformed", "engineered" or "modified for exogenous gene expression" are used interchangeably herein.

The terms "recombinant construct", "expression construct", "recombinant expression construct" and "expression cassette" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The terms "production host", "host" and "host cell" are used interchangeably herein and refer to any organism, or cell thereof, whether human or non-human into which a recombinant construct can be stably or transiently introduced in order to express a gene. This term encompasses any progeny of a parent cell, which is not identical to the parent cell due to mutations that occur during propagation.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cut-off=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25 (17): 3389-402). Using this information, proteins sequences can be grouped. A phylogenetic tree can be built using the amino acid sequences.

Sequence alignments and percent identity calculations may be performed using the Megalign program of the LASERGENE bioinformatics computing suite (DNASTAR Inc., Madison, WI), the AlignX program of Vector NTI v. 7.0 (Informax, Inc., Bethesda, MD), or the EMBOSS Open Software Suite (EMBL-EBI; Rice et al., *Trends in Genetics* 16, (6): 276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13): 3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1. In one embodiment, a fast or slow alignment is used with the default settings where a slow alignment. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Various polypeptide amino acid sequences and polynucleotide sequences are disclosed herein as features of certain aspects. Variants of these sequences that are at least about 70-85%, 85-90%, or 90%-95% identical to the sequences disclosed herein may be used in certain embodiments. Alternatively, a variant polypeptide sequence or polynucleotide sequence in certain embodiments can have at least 60%, 61%, 62%, 63%, 64%, 65%, 66%, 67%, 68%,69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

The term "variant", with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. The terms "expression cassette" and "expression vector are used interchangeably herein and refer to a specific vector containing a gene and having elements in addition to the gene that allow for expression of that gene in a host.

The term "expression", as used herein, refers to the production of a functional end-product (e.g., an mRNA or a protein) in either precursor or mature form. Expression may also refer to translation of mRNA into a polypeptide.

Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals. "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms The expression vector can be one of any number of vectors or cassettes useful for the transformation of suitable production hosts known in the art. Typically, the vector or cassette will include sequences directing transcription and translation of the relevant gene, a selectable marker, and sequences allowing autonomous replication or chromosomal integration. Suitable vectors generally include a region 5' of the gene which harbors transcriptional initiation controls and a region 3' of the DNA fragment which controls transcriptional termination. Both control regions can be derived from homologous genes to genes of a transformed production host cell and/or genes native to the production host, although such control regions need not be so derived.

As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25 (17): 3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

As used herein, the term "functional assay" refers to an assay that provides an indication of an enzyme's activity. In some embodiments, the term refers to assay systems in which an enzyme is analyzed for its ability to function in its usual capacity.

Ruminants have the unique ability to convert roughage into protein and energy through their microbial/enzyme digestive systems. Accordingly, ruminants play an important role in the earth's ecology and in the food chain.

The primary difference between a ruminant and a non-ruminant is that a ruminant has a four-compartment stomach consisting of a rumen, reticulum, omasum and abomasum. The abomasum is the direct equivalent of the monogastric stomach (McDonald et al., 2011, Animal Nutrition (7th Edition), pages 156-191).

The rumen is the largest compartment, with a volume of 150-200 litres (40-50 gallons).

In the digestive system there are billions of microorganisms. They help the cow to digest and utilize nutrients in the feed. To achieve efficient feed utilization and high milk yield, the bacteria must have optimal conditions. It is the bacteria that digest the feed. Feeding a cow, in fact, involves feeding the micro-organisms in her rumen.

The process of fermentation takes place in the rumen and the reticulum. The cow's rumen is like a large fermentation vat. More than 200 different bacteria and 20 types of protozoa help the cow to utilize fibrous feedstuffs and non-protein nitrogen sources.

Fermentation is when microorganisms convert carbohydrates into volatile fatty acids and gases. This process allows the cow to convert cellulosic fiber into energy.

Of gases produced within the rumen during fermentation (500-1500 litres per day) (150-400 gallons), 20-40% consist of methane and carbon dioxide. Production of fermentation gases represents a considerable energy loss. Certain fermentation modifiers, such as ionophores, improve energy efficiency of ruminants by reducing those gas energy losses.

The fermentation gases are expelled by belching. When belching is impossible or ineffective, cows can suffer from bloat. When feed enters the rumen it is layered upon the rumen mat which floats upon the top of the rumen contents. Through rhythmic contractions of the ruminal wall, the freshly eaten material accumulates at the rear area of the mat. The rumen mat consists of non-digested material with a 15% dry matter content. Bacteria adhere to the feed and gradually digest the fermentable material. When the cow ruminates, cuds from the front layer are eructed. Saliva is added in the mouth and through the grinding action of the teeth, the surfaces exposed to micro-organisms become larger.

The feed particles become smaller as the bacteria work and the rumination process continues. They gradually absorb fluid and sink to the bottom of the rumen. The rumen contents in the bottom of the reticulo-rumen have a dry matter content of 5%.

The rumen contracts once every minute. The contractions allow mixing of fluid and solid contents in the rumen to stimulate fermentation and avoid stagnation. Contractions also serve to release gases trapped in either the mat or fluid portion of the ruminal contents. The fermentation gases are then released by belching. Disruption of this process can result in bloat. Feed particles of the correct size and density are segregated into the fluid in the reticulum by the ruminal contractions. Subsequent contractions force these particles and some of the fluid contents out of the reticulo-rumen and into the omasum.

The rumen and reticulum are basically one compartment, but with different functions. While much of fermentative action occurs in the rumen, the reticulum serves as a staging area for passage into the omasum or regurgitation.

The ideal rumen pH value is between 6 and 7. The ruminal microorganisms are healthiest within this range. If the pH value varies too much, some types of micro-organisms are eliminated, and there is reduced utilization of the feed. Micro-organisms that digest cellulose (hay, silage, etc.) are unable to grow or ferment cellulose with a pH value below 6.0. When ruminal pH drops below 6, the rumen is considered to be acidotic. Ruminal acidosis can be acute with a rapid, severe drop in pH. More common in high producing herds is sub-clinical acidosis which is characterized by chronic, intermittent periods of low ruminal pH.

As was noted above, the digestibility of starch in feeds is highly variable and dependent on a number of factors including the physical structure of both the starch and feed matrix.

It has been found that starch digestibility, especially the hydrolysis of raw starch, in a ruminant's diet can be improved by the use of at least one alpha-1,4/1,6-glycoside hydrolase (GLCH) as a feed additive for a ruminant wherein said hydrolase: (a) has at least 20% activity at pH less than or equal to 3 in the presence of pepsin as compared to activity of the enzymes at pH 6 in the presence of pepsin, (b) said hydrolases active in at least two digestive chambers of a ruminant comprising a rumen, a reticulum, an omasum and an abomasum and (c) the hydrolase works with digestive enzymes present in the digestive chambers of the ruminant to increase glucose yield and increase starch digestibility.

In yet another aspect, there is described a method for increasing starch digestibility, increasing glucose yield, increase dry matter digestion and increase gas production during fermentation in a ruminant comprising adding to the feed an enzyme composition comprising (i) at least one GLCH enzyme as a feed additive for a ruminant wherein said enzyme: (a) has at least 20% activity at pH less than or equal to 3 in the presence of pepsin as compared to activity of the enzymes at pH 6 in the presence of pepsin, (b) said enzyme is active in at least two of three digestive chambers of a ruminant comprising a rumen, an abomasum and a small intestine and (c) the enzyme works with pancreatic amylase to increase glucose yield and (ii) at least one protease.

Some digestive enzymes present in the digestive chambers of a ruminant with which the hydrolase can work to increase glucose yield include, but are not limited to, ruminal microbial amylolytic enzymes, pepsin or pancreatin.

Preferably, the hydrolase is capable of hydrolyzing raw starch under conditions comparable to conditions found in the rumen or abomasum.

The hydrolase can be selected from the group consisting of alpha-amylases, glucoamylases and alpha-glucosidases or the hydrolase is selected from the group consisting of alpha-amylases and glucoamylases.

Any suitable alpha-amylase (E.C. 3.2.1.1), whether or not commercially available, can be used in the method described herein.

Exemplary alpha-amylases include, but are not limited to, a wild-type alpha-amylase, a variant or fragment thereof or a genetically engineered hybrid alpha-amylase which is derived from, for example, a catalytic domain from one microbial source and a starch binding domain from another microbial source. Non-limiting examples of other alpha-amylases that can be useful to make such hybrids can be derived from *Bacillus, Aspergillus, Trichoderma, Rhizopus, Fusarium, Penicillium, Neurospora* and *Humicola*.

There can also be mentioned those alpha-amylases having granular starch hydrolyzing activity (GSH) or alpha-amylases that have been recombinantly engineered to have GSH activity. Such GSH activity is advantageous because these enzymes break down more of the starch, particularly any granular (raw) starch, which may be present in any feed containing molasses and the like. Alpha-amylases having GSH activity include, but are not limited to, alpha-amylases obtained from *Aspergillus kawachi* (e.g., AkAA), *Aspergillus niger* (e.g., AnAA), *A. clavatus* (AcAA), *A. terreus* (AtAA), and *Trichoderma reesei* (e.g., TrAA).

Alpha-amylases, AkAA, AcAA, and AtAA, have two carbohydrate binding domains, one of which belongs to carbohydrate binding module/domain family 20 (CBM20 or CD20) while the other is sometimes called a secondary binding site (SBS). SBSs and CBMs appear to function by 1) targeting the enzyme towards its substrate, 2) guiding the substrate into the active site groove, 3) substrate disruption, 4) enhancing processivity, 5) allosteric regulation, 6) passing on reaction products, and/or 7) anchoring to the cell wall of the parent microorganism.

Many of these putative functions agree with the functions ascribed to non-catalytic binding in CBMs. In contrast to CBMs, SBSs have a fixed position relative to the catalytic site, making them more or less suitable to take up specific functions (Cuyvers S., Dornez E., Delcour J. A., Courtin C. M. (2012), Occurrence and functional significance of secondary carbohydrate binding sites in glycoside hydrolases. Crit. Rev. Biotechnol. 32, 93-107).

Some commercially available alpha-amylases that may have GSH activity or enzymes used in carbohydrate hydrolysis processes are commercially available, see, e.g., TERMAMYL® 120-L, LC and SC SAN SUPER®, SUPRA®, and LIQUEZYME® SC available from Novo Nordisk A/S, FUELZYME® LF from Verenium, and CLARASE® L, SPEZYME® FRED, SPEZYME® XTRA, GC626, and GZYME® G997 available from Danisco, US, Inc., Genencor Division.

In other embodiments, it is desirable that the alpha-amylase be an acid stable alpha-amylase having 20% activity at pH less than or equal to 3.0 compared to its activity at pH6.0

Alpha-amylases can be selected from the group consisting of alpha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC3.2.1.60); isoamylase (EC 3.2.1.68); glucodextranase (EC 3.2.1.70); maltohexaose-forming alpha-amylase (EC 3.2.1.98); maltotriose-forming alpha-amylase (EC 3.2.1.116); branching enzyme (EC 2.4.1.18); trehalose synthase (EC 5.4.99.16); 4-alpha-glucanotransferase (EC 2.4.1.25); maltopentaose-forming alpha-amylase (EC 3.2.1.-); amylosucrase (EC 2.4.1.4); sucrose phosphorylase (EC 2.4.1.7); malto-oligosyltrehalose trehalohydrolase (EC 3.2.1.141); isomaltulose synthase (EC 5.4.99.11); malto-oligosyltrehalose synthase (EC 5.4.99.15); amylo-alpha-1,6-glucosidase (EC 3.2.1.33); and alpha-1,4-glucan: phosphate alpha-maltosyltransferase (EC 2.4.99.16);

Any suitable glucoamylase (GA) (E.C. 3.2.1.3.), whether or not commercially available, can be used in the method described herein.

Suitability of a glucoamylase (syn. amyloglucosidase (GA) (E.C. 3.2.1.3) will depend upon its activity toward maltose. Thus, a suitable glucoamylase should have at least 20% of the activity on maltose on a protein basis compared to the activity of glucoamylase obtained from *Trichoderma reesei* (TrGA) when assayed at 2% (w/v) maltose, pH6.0 and 40° C. TrGA is widely used in first generation bioethanol processing due to its glucose generating capabilities from starch (US patent, 2008, U.S. Pat. No. 7,413,879 B2, *Trichoderma reesei* glucoamylase and homologs thereof). STARGEN™ 002 is a granular starch hydrolyzing enzyme product for ethanol production sold by DuPont.

It is important for animal nutrition that the hydrolysis rate of maltose to glucose be high since it is glucose that is absorbed by the blood stream in the digestive tract, not its corresponding dimer, maltose.

Thus, the low activity of *Aspergillus niger* glucoamylase (AnGA) on maltose makes it an unsuitable glucoamylase to use in the methods described here. Glucoamylase is known to have many subsites for binding near the active site. A subsite theory was developed for analyzing the substrate affinities of glucoamylases. One of the assumptions of this theory is that a substrate can be bound to the enzyme in either a productive or a nonproductive mode. It is believed that the low activity of *Aspergillus niger* glucoamylase (AnGA) may be due to the likelihood that maltose is binding to AnGA in a nonproductive mode. (Swanson et al., 1977, Biotechnol. Bioeng. 19:1715-1718).

Exemplary glucoamylases include, but are not limited to, a wild-type glucoamylases, a variant or fragment thereof or a genetically engineered hybrid glucoamylase which can be derived from, for example, a catalytic domain from one microbial source and a starch binding domain from another microbial source. Hybrid glucoamylase include, for example, glucoamylases having a catalytic domain from a GA from one organism (e.g., *Talaromyces* GA) and a starch binding domain (SBD) from a different organism (e.g.; *Trichoderma* GA).

Such hybrid glucoamylases can also be made using a peptide to line a catalytic domain from a GA from one organism (e.g., *Talaromyces* GA) and a starch binding domain (SBD) from a different organism (e.g.; *Trichoderma* GA).

Examples of such hybrid glucoamylases include, but are not limited to *Aspergillus niger* G1 and G2 glucoamylase (See e.g., Boel et al., (1984) EMBO J. 3:1097-1102; WO 92/00381, WO 00/04136 and U.S. Pat. No. 6,352,851); *Aspergillus awamori* glucoamylases (See e.g., WO 84/02921); *Aspergillus oryzae* glucoamylases (See e.g., Hata et al., (1991) Agric. Biol. Chem. 55:941-949) and *Aspergillus shirousami*. (See e.g., Chen et al., (1996) Prot. Eng. 9:499-505; Chen et al. (1995) Prot. Eng. 8:575-582; and Chen et al., (1994) Biochem J. 302:275-281).

Some glucoamylases are endogenously expressed by bacteria, plants, and/or fungi. For example, some glucoamylases are produced by several strains of filamentous fungi.

Preferably, the glucoamylase will have granular starch hydrolyzing activity (GSH) or have been recombinantly engineered to have GSH activity. Such GSH activity is advantageous because these enzymes break down more of the starch, particularly any granular (raw) starch, which may be present in any feed containing molasses and the like.

Glucoamylases that can be used in the method disclosed herein include those obtained from strains of *Talaromyces* ((e.g., *T. emersonii, T. leycettanus, T. duponti* and *T. thermophilus* glucoamylases (See e.g., WO 99/28488; U.S. Pat. No. RE: 32,153; U.S. Pat. No. 4,587,215)); strains of *Trichoderma*, (e.g., *T. reesei*) and glucoamylases having at least about 80%, about 85%, about 90% and about 95% sequence identity to SEQ ID NO: 4 disclosed in US Pat. Pub. No. 2006-0094080; strains of *Rhizopus*, (e.g., *R. niveus* and *R. oryzae*); strains of *Mucor* and strains of *Humicola*, ((e.g., *H. grisea* (See, e.g., Boel et al., (1984) EMBO J. 3:1097-1102; WO 92/00381; WO 00/04136; Chen et al., (1996) Prot. Eng. 9:499-505; Taylor et al., (1978) Carbohydrate Res. 61:301-308; U.S. Pat. Nos. 4,514,496; 4,092,434; 4,618,579; Jensen et al., (1988) Can. J. Microbiol. 34:218-223 and SEQ ID NO: 3 of WO 2005/052148)). In some embodiments, the glucoamylase has at least about 85%, about 90%, about 92%, about 94%, about 95%, about 96%, about 97%, about 98% and about 99% sequence identity to the amino acid sequence of SEQ ID NO: 3 of WO 05/052148. Other glucoamylases useful in the present invention include those obtained from *Athelia rolfsii* and variants thereof (See e.g., WO 04/111218) and *Penicillium* spp. (e.g., *Penicillium chrysogenum*).

Commercially available glucoamylases include but are not limited to Spirizyme Ultra, Spirizyme® Achieve, Spirizyme® Fuel, SPIRIZYME® EXCEL, DISTILLASE®, OPTIDEX® L-400 and G ZYME® G990 4X, GC480, G-ZYME® 480, FERMGEN® 1-400 (Danisco US, Inc, Genencor Division), CU.CONC® (Shin Nihon Chemicals, Japan), GLUCZYME® (Amano Pharmaceuticals, Japan (See e.g. Takahashi et al., (1985) J. Biochem. 98:663-671)). Secondary enzymes that find use in the invention include three forms of glucoamylase (e.g., E.C.3.2.1.3) produced by a *Rhizopus* sp., namely "Gluc1" (MW 74,000), "Gluc2" (MW 58,600) and "Gluc3" (MW 61,400).

Any suitable alpha-glucosidase (E.C.3.2.1.20) can be used as described herein.

As was noted above, alpha-glucosidase releases glucose from maltose, isomaltose and maltosaccharides in its hydrolytic mode. It can also transfer glucose unit to acceptor molecules including glucose, maltose, isomaltose and maltosaccharides or any other suitable molecules in its synthetic mode, especially at higher substrate concentration and high product concentration. In the digestive tract, the synthetic mode or transferring reaction is minimal as product glucose generated will be removed due to absorption.

Proteases (also called peptidases or proteinases) are enzymes capable of cleaving peptide bonds. Proteases have evolved multiple times, and different classes of proteases can perform the same reaction by completely different catalytic mechanisms. Proteases can be found in animals, plants, bacteria, archaea and viruses.

Proteolysis can be achieved by enzymes currently classified into six broad groups: aspartic proteases, cysteine proteases, serine proteases, threonine proteases, glutamic proteases, and metalloproteases.

Preferably, the protease is an acid protease and, more preferably it is an acid fungal protease.

Any acid or neutral proteases can be used in this disclosure. For example, acid fungal proteases include those obtained from *Aspergillus, Trichoderma, Mucor* and *Rhizopus*, such as *A. niger, A. awamori, A. oryzae, Trichoderma reesei*, and *M. miehei*. AFP can be derived from heterologous or endogenous protein expression of bacteria, plants and fungi sources. Preferably, the AFP is secreted from strains of *Trichoderma*.

Exemplary acid proteases include, but are not limited to, a wild-type acid protease, a variant or fragment thereof or a genetically engineered hybrid acid protease which can be derived from, for example, a catalytic domain from one microbial source and a starch binding domain from another microbial source.

In another aspect, the protease can be a neutral protease such as a metalloprotease (syn. Metallopeptidase), and, more preferably, a bacterial metalloprotease.

In another aspect any isolated, recombinant, substantially pure, synthetically derived, or non-naturally occurring nucleic acid comprising a nucleotide sequence encoding any polypeptide having any of the glycoside hydrolase activities described herein (including any fusion protein, etc.) that has been discussed hereinabove. Also of interest is a vector comprising a polynucleotide encoding any of the glycoside hydrolases described herein. It will be apparent to the skilled person that the vector can be any suitable expression vector and that the choice of vector may vary depending upon the type of cell into which the vector is to be inserted. Suitable vectors include pGAPT-PG, pRAX1, pGAMD, pGPT-pyrG1, pC194, pJH101, pE194, and pHP13 (See, Harwood and Cutting [eds.], Chapter 3, Molecular Biological Methods for *Bacillus*, John Wiley & Sons [1990]). See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

The expression vector can be one of any number of vectors or cassettes useful for the transformation of suitable production hosts known in the art. Typically, the vector or cassette will include sequences directing transcription and translation of the relevant gene, a selectable marker, and sequences allowing autonomous replication or chromosomal integration. Suitable vectors generally include a region 5' of the gene which harbors transcriptional initiation controls and a region 3' of the DNA fragment which controls transcriptional termination. Both control regions can be derived from homologous genes to genes of a transformed production host cell and/or genes native to the production host, although such control regions need not be so derived.

DNA fragments which control transcriptional termination may also be derived from various genes native to a preferred production host cell. In certain embodiments, the inclusion of a termination control region is optional. In certain embodiments, the expression vector includes a termination control region derived from the preferred host cell.

The expression vector can be included in the production host, particularly in the cells of microbial production hosts. The production host cells can be microbial hosts found within the fungal or bacterial families and which grow over a wide range of temperature, pH values, and solvent tolerances. For example, it is contemplated that any of bacteria, algae, and fungi such as filamentous fungi and yeast may suitably host the expression vector.

Inclusion of the expression vector in the production host cell may be used to express the protein of interest so that it may reside intracellularly, extracellularly, or a combination of both inside and outside the cell. Extracellular expression renders recovery of the desired protein from a fermentation product more facile than methods for recovery of protein produced by intracellular expression.

The recombinant expression vector may be any vector such as a plasmid or virus which can conveniently be subjected to recombinant DNA procedures and lead to expression of the nucleotide sequence. The vector choice will typically depend on the compatibility of the vector with the production host into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the production host, is integrated into the genome and replicated together with the chromosome(s) into which it has been integrated. Some non-limiting examples of such vectors is provided in the Fungal Genetics Stock Center Catalogue of Strains (FGSC, worldwideweb.fgsc.net), Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press. 396-428 and U.S. Pat. No. 5,874,276. Particularly useful vectors include pTREX, pFB6, pBR322, PUCI8, pUCI00 and pENTR/D. Suitable plasmids for use in bacterial cells include pBR322 and pUC19 permitting replication in *E. coli* and pE194 for example permitting replication in *Bacillus*.

Briefly with respect to production in production host cells reference can be made to Sambrook et al., (1989) supra, Ausubel (1987) supra, van den Hondel et al. (1991) in Bennett and Lasure (Eds.) MORE GENE MANIPULATIONS IN FUNGI, Academic Press (1991) pp. 70-76 and 396-428; Nunberg et al., (1984) *Mol. Cell Biol.* 4:2306-2315; Boel et al., (1984) 30 *EMBO J.* 3:1581-1585; Finkelstein in BIOTECHNOLOGY OF FILAMENTOUS FUNGI, Finkelstein et al. Eds. Butterworth-Heinemann, Boston, MA (1992), Chap. 6; Kinghorn et al. (1992) APPLIED MOLECULAR GENETICS OF FILAMENTOUS FUNGI, Blackie Academic and Professional, Chapman and Hall, London; Kelley et al., (1985) *EMBO J.* 4:475-479; Penttila et al., (1987) *Gene* 61:155-164; and U.S. Pat. No. 5,874,276. A list of suitable vectors may be found in the Fungal Genetics Stock Center Catalogue of Strains (FGSC, worldwideweb.fgsc.net). Suitable vectors include those obtained from for example Invitrogen Life Technologies and Promega. Specific vectors suitable for use in fungal host cells include vectors such as pFB6, pBR322, pUC 18, pUC100, pDON™201, pDONR™221, pENTR™, pGEM®3Z and pGEM®4Z.

The vector system may be a single vector or plasmid or two or more vectors or plasmids which together contain the total DNA to be introduced into the genome of the host cell, or a transposon.

The vector may also contain one or more selectable markers to permit easy selection of the transformed cells. A selectable marker is a gene, the product of which provides for biocide or viral resistance and the like. Examples of selectable markers include ones which confer antimicrobial resistance. Nutritional markers also find use in the present invention including those markers known in the art as amdS, argB and pyr4. Markers useful for the transformation of *Trichoderma* are known in the art (see, e.g., Finkelstein, chapter 6, in Biotechnology of Filamentous Fungi, Finkelstein et al., EDS Butterworth-Heinemann, Boston MA (1992) and Kinghorn et al., (1992) Applied Molecular Genetics of Filamentous Fungi, Blackie Academic and Professional, Chapman and Hall, London). In some embodiments, the expression vectors will also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical; any of the many resistance genes known in the art are suitable. The prokaryotic sequences are preferably chosen such that they do not interfere with the replication or integration of the DNA in *Trichoderma reesei*.

The vector may also contain an element(s) permitting stable integration of the vector into the product host genome or autonomous replication of the vector in the production host independent of the genome of the cell. For integration into the host cell genome, the vector may rely on the nucleotide sequence encoding the aspartic protease or any other element of the vector for stable integration of the vector into the genome by homologous or nonhomologous recombination.

For autonomous replication, the vector may further comprise an origin of replication enabling the vector to replicate autonomously in the production host.

More than one copy of the nucleotide sequence encoding a glycoside hydrolase may be inserted into the production host to increase production thereof. An increase in the copy number of the nucleotide sequence can be obtained by integrating at least one additional copy of the sequence into the genome of the production host or by including an amplifiable selectable marker gene, and thereby additional copies of the nucleotide sequence can be selected for by culturing the production host cells in the presence of an appropriate selectable agent.

A vector comprising the nucleotide sequence encoding any of the glycoside hydrolases is introduced into the production host so that the vector is maintained as a chromosomal integrant or as a self-replicating extra-chromosomal vector. Integration is generally considered to be an advantage as the nucleotide sequence is more likely to be stably maintained the production host. Integration of the vector into the production host chromosome may occur by homologous or non-homologous recombination as was discussed above.

Exemplary vectors include, but are not limited to pGXT (the same as the pTTTpyr2 vector as described in published PCT application WO2015/017256). There can also be mentioned standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Examples of suitable expression and/or integration vectors are provided in Sambrook et al., (1989) supra, Bennett and Lasure (Eds.) More Gene Manipulations in Fungi, (1991) Academic Press pp. 70-76 and pp. 396-428 and articles cited therein; U.S. Pat. No. 5,874,276 and Fungal Genetic Stock Center Catalogue of Strains, (FGSC, worldwideweb.fgsc.net.). Useful vectors may be obtained from Promega and Invitrogen. Some specific useful vectors include pBR322, pUC18, pUC100, pDON™201, pENTR™, pGEN®3Z and pGEN®4Z. However, other forms of expression vectors which serve equivalent functions and which are, or become, known in the art can also be used. Thus, a wide variety of host/expression vector combinations may be employed in expressing the DNA sequences disclosed herein. Useful expression vectors, for example, may consist of segments of chromosomal, non-chromosomal and synthetic DNA sequences such as various known derivatives of SV40 and known bacterial plasmids, e.g., plasmids from E. coli including col E1, pCR1, pBR322, pMb9, pUC 19 and their derivatives, wider host range plasmids, e.g., RP4, phage DNAs e.g., the numerous derivatives of phage.lambda., e.g., NM989, and other DNA phages, e.g., M13 and filamentous single stranded DNA phages, yeast plasmids such as the 2.mu plasmid or derivatives thereof.

The choice of a production host can be any suitable microorganism such as bacteria, fungi and algae. Typically, the choice will depend upon the gene encoding the glycoside hydrolase of interest.

Examples of suitable production hosts include, but are not limited to, bacterial, fungal, plant cells etc. Preferably, the production host may be selected from E. coli, Streptomyces, Hansenula, Trichoderma (particularly T. reesei), Bacillus, Lactobacillus, Aspergillus (particularly A. niger), a plant cell and/or spores of Bacillus, Trichoderma, or Aspergillus.

In some embodiments, a recombinant glycoside hydrolase enzyme may be used in the methods and compositions disclosed herein. In a preferred aspect, there is provided a food or feed additive comprising the glycoside hydrolase described herein.

Many standard transfection methods can be used to produce bacterial and filamentous fungal (e.g. Aspergillus or Trichoderma) cell lines that express large quantities of the desired glycoside hydrolase. Some of the published methods for the introduction of DNA constructs into cellulase-producing strains of Trichoderma include Lorito, Hayes, DiPietro and Harman, (1993) Curr. Genet. 24:349-356; Goldman, VanMontagu and Herrera-Estrella, (1990) Curr. Genet. 17:169-174; and Penttila, Nevalainen, Ratto, Salminen and Knowles, (1987) Gene 6:155-164, also see USP 6,022,725; U.S. Pat. No. 6,268,328 and Nevalainen et al., "The Molecular Biology of Trichoderma and its Application to the Expression of Both Homologous and Heterologous Genes" in Molecular Industrial Mycology, Eds, Leong and Berka, Marcel Dekker Inc., NY (1992) pp 129-148; for Aspergillus include Yelton, Hamer and Timberlake, (1984) Proc. Natl. Acad. Sci. USA 81:1470-1474, for Fusarium include Bajar, Podila and Kolattukudy, (1991) Proc. Natl. Acad. Sci. USA 88:8202-8212, for Streptomyces include Hopwood et al., 1985, Genetic Manipulation of Streptomyces: Laboratory Manual, The John Innes Foundation, Norwich, UK and Fernandez-Abalos et al., Microbiol 149:1623-1632 (2003) and for Bacillus include Brigidi, DeRossi, Bertarini, Riccardi and Matteuzzi, (1990) FEMS Microbiol. Lett. 55:135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). Also of use is the Agrobacterium-mediated transfection method described in U.S. Pat. No. 6,255,115. It is only necessary that the particular genetic engineering procedure used be capable of successfully introducing at least one gene into the host cell capable of expressing the gene.

Depending upon the host cell used post-transcriptional and/or post-translational modifications may be made. One non-limiting example of a post-transcriptional and/or post-translational modification is "clipping" or "truncation" of a polypeptide. For example, this may result in taking a glycoside hydrolase from an inactive or substantially inactive state to an active state as in the case of a pro-peptide undergoing further post-translational processing to a mature peptide having the enzymatic activity. In another instance, this clipping may result in taking a mature a glycoside hydrolase as described herein and further removing N or C-terminal amino acids to generate truncated forms that retain enzymatic activity.

Other examples of post-transcriptional or post-translational modifications include, but are not limited to, myristoylation, glycosylation, truncation, lipidation and tyrosine, serine or threonine phosphorylation. The skilled person will appreciate that the type of post-transcriptional or post-translational modifications that a protein may undergo may depend on the host organism in which the protein is expressed.

Transformation methods for Aspergillus and Trichoderma are described in, for example, Yelton et al. (1984) Proc. Natl. Acad. Sci. USA 81:1470-1474; Berka et al., (1991) in Applications of Enzyme Biotechnology, Eds. Kelly and Baldwin, Plenum Press (NY); Cao et al., (2000) Sci. 9:991-1001; Campbell et al., (1989) Curro Genet. 16:53-56; Pentilla et al., (1987) Gene 61:155-164); de Groot et al., (1998) Nat. Biotechnol. 16:839 842; U.S. Pat. Nos. 6,022,725; 6,268,328 and EP 238 023. The expression of heterologous protein in Trichoderma is described in U.S. Pat. Nos. 6,022,725; 6,268,328; Harkki et ale (1991); Enzyme Microb.

*Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to WO96100787 and Bajar et al., (1991) Proc. Natl. Acad. Sci. USA 88:8202-28212 for transformation of *Fusarium* strains.

After the expression vector is introduced into the cells, the transfected or transformed cells are cultured under conditions favoring expression of genes under control of the promoter sequences. In some instances, the promoter sequence is the cbh1 promoter. Large batches of transformed cells can be cultured as described in Ilmen et al 1997 ("Regulation of cellulase gene expression in the filamentous fungus *Trichoderma reesei*." Appl. Envir. Microbiol. 63:1298-1306).

Uptake of DNA into the host *Trichoderma* sp. strain depends upon the calcium ion concentration. Generally, about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethyleneglycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2 \times 10^6$/mL. A volume of 100 μL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

The medium used to cultivate the cells may be any conventional medium suitable for growing the host cell and obtaining expression of any of the glycoside hydrolases described herein. Suitable media and media components are available from commercial suppliers or may be prepared according to published recipes (e.g., as described in catalogues of the American Type Culture Collection).

In some embodiments, the preparation of a spent whole fermentation broth of a recombinant microorganism can be achieved using any cultivation method known in the art resulting in the expression of enzyme of interest. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the enzyme to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

Host cells may be cultured under suitable conditions that allow expression of any of the glycoside hydrolases described herein. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or sophorose.

Polypeptides can also be produced recombinantly in an in vitro cell-free system, such as the TNT™ (Promega) rabbit reticulocyte system. An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired alpha-glucosidase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of the enzyme of interest as the glycoside hydrolase described herein. Since production hosts and transformed cells can be cultured in conventional nutrient media. The culture media for transformed host cells may be modified as appropriate for activating promoters and selecting transformed cells. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; worldwideweb.atcc.org).

Any of the fermentation methods well known in the art can suitably be used to ferment the transformed or the derivative fungal strain as described above.

A classical batch fermentation is a closed system, where the composition of the medium is set at the beginning of the fermentation, and the composition is not altered during the fermentation. At the beginning of the fermentation, the medium is inoculated with the desired organism(s). In other words, the entire fermentation process takes place without addition of any components to the fermentation system throughout.

Alternatively, a batch fermentation qualifies as a "batch" with respect to the addition of the carbon source. Moreover, attempts are often made to control factors such as pH and oxygen concentration throughout the fermentation process. Typically, the metabolite and biomass compositions of the batch system change constantly up to the time the fermentation is stopped. Within batch cultures, cells progress through a static lag phase to a high growth log phase and finally to a stationary phase, where growth rate is diminished or halted. Left untreated, cells in the stationary phase would eventually die. In general, cells in log phase are responsible for the bulk of production of product. A suitable variation on the standard batch system is the "fed-batch fermentation" system. In this variation of a typical batch system, the substrate is added in increments as the fermentation progresses. Fed-batch systems are useful when it is known that catabolite repression would inhibit the metabolism of the cells, and/or where it is desirable to have limited amounts of substrates in the fermentation medium. Measurement of the actual substrate concentration in fed-batch systems is difficult and is therefore estimated on the basis of the changes of measurable factors, such as pH, dissolved oxygen and the partial pressure of waste gases, such as CO2. Batch and fed-batch fermentations are well known in the art.

Continuous fermentation is another known method of fermentation. It is an open system where a defined fermentation medium is added continuously to a bioreactor, and an equal amount of conditioned medium is removed simultaneously for processing. Continuous fermentation generally maintains the cultures at a constant density, where cells are maintained primarily in log phase growth. Continuous fermentation allows for the modulation of one or more factors that affect cell growth and/or product concentration. For example, a limiting nutrient, such as the carbon source or nitrogen source, can be maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Separation and concentration techniques are known in the art and conventional methods can be used to prepare a concentrated solution or broth comprising an alpha-glucosidase polypeptide of the invention.

After fermentation, a fermentation broth is obtained, the microbial cells and various suspended solids, including residual raw fermentation materials, are removed by conventional separation techniques in order to obtain an enzyme-containing solution. Filtration, centrifugation, microfiltration, rotary vacuum drum filtration, ultrafiltration, centrifugation followed by ultra-filtration, extraction, or chromatography, or the like, are generally used.

It may at times be desirable to concentrate a solution or broth comprising the polypeptide of interest to optimize recovery. Use of un-concentrated solutions or broth would typically increase incubation time in order to collect the enriched or purified enzyme precipitate.

The enzyme-containing solution can be concentrated using conventional concentration techniques until the desired enzyme level is obtained. Concentration of the enzyme containing solution may be achieved by any of the techniques discussed herein. Examples of methods of enrichment and purification include but are not limited to rotary vacuum filtration and/or ultrafiltration.

A glycoside hydrolase as described herein as described herein can be tested for activity using a variety of tests known in the art. For example, activity can be tested by combining the enzyme with glycoprotein or oligosaccharide and water as necessary. Activity can be measured by analysis of reaction products, which can be separated and visualized, for example, by thin layer chromatography, or by HPLC using columns for monosaccharides and oligosaccharides analysis, coupled enzyme assay using glucose oxidase-peroxidase for glucose quantification and 3,5-dinitrosalicylic acid (DNS) reagent for general reducing sugar assay (see Examples below).

In addition, a glycoside hydrolase as described herein whether or not encapsulated, may be in the form of a granule.

It is believed that a glycoside hydrolase as described herein may be used in combination with one or more additional enzymes. In some embodiments, the one or more additional enzymes, esterases, formamidase, -galactosidases, for example □ or □-galactosidases, exo-glucanases, glucan lyases, endo-glucanases, glucoamylases, glucose oxidases, glucosidases, for example □ or □-glucosidases, glucuronidases, hemicellulases, hydrolases, invertases, isomerases, laccases, phenol oxidases, lipase, lyases, mannosidases, oxidases, oxidoreductases, pectinase, pectate lyases, pectin acetyl esterases, pectin depolymerases, peptidase, pectin methyl esterases, pectinolytic enzymes, peroxidases, phenoloxidases, phytase, polygalacturonases, rhamno-galacturonases, ribonucleases, thaumatin, transferases, transport proteins, transglutaminases, xylanases, hexose oxidase (D-hexose: (3/4-oxidoreductase, EC 1.1.3.5), acid phosphatases and/or others or combinations thereof. These include enzymes that, for example, modulate the viscosity of the composition or feed.

Any of the GLCH enzymes discussed herein, preferably, alpha-amylases, glucoamylases and alpha-glucosidases may be used in combination with a direct fed microbial. Categories of DFMs include *Bacillus*, Lactic Acid Bacteria and Yeasts. Bacilli are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets. Types of Lactic Acid Bacteria include *Bifidobacterium, Lactobacillus* and *Streptococcus*. Yeasts are not bacteria. These microorganisms belong to the plant group fungi.

Any of the GLCH enzymes discussed herein, preferably, alpha-amylases, glucoamylases and alpha-glucosidases may be used in combination with suitable veterinary drugs to reduce acidosis or to reduce ruminal protozoa organisms.

Such veterinary drugs may include ionophores, such as monensin and its derivatives.

Toxin binders are designed to bind toxins in feed and protect animals from their ill effects. Accordingly, any of the GLCH enzymes discussed herein may also be used in combination with toxin binders or toxin adsorbents. An example of a toxin binder is a mycotoxin binder including, but not limited to, different hydrated sodium calcium aluminosilicates (HSCAS), bentonite, zeolite, clays, yeast cell walls and toxin degrading enzymes.

In another aspect, any of the GLCH enzymes discussed herein may also be used in combination with herbs, essential oils, and anticaking agents.

An essential oil is a concentrated hydrophobic liquid containing volatile aroma compounds from plants. Essential oils are also known as volatile oils, ethereal oils, aetherolea, or simply as the oil of the plant from which they were extracted, such as oil of clove. An oil is "essential" in the sense that it contains the "essence of" the plant's fragrance—the characteristic fragrance of the plant from which it is derived. The term essential used here does not mean indispensable as with the terms essential amino acid or essential fatty acid which are so called since they are nutritionally required by a given living organism. Essential oils are generally extracted by distillation, often by using steam. Other processes include expression, solvent extraction, absolute oil extraction, resin tapping, and cold pressing. They are used in perfumes, cosmetics, soaps and other products, for flavoring food and drink, and for adding scents to incense and household cleaning products.

Animal feeds may include plant material such as corn, wheat, sorghum, soybean, canola, sunflower or mixtures of any of these plant materials or plant protein sources for ruminants. It is contemplated that animal performance parameters, such as growth, feed intake and feed efficiency, but also improved uniformity, reduced ammonia concentration in the animal house and consequently improved welfare and health status of the animals will be improved. More specifically, as used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by an animal's ability to avoid the negative effects of necrotic enteritis and/or by the immune response of the subject.

The terms "animal feed," "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

When used as, or in the preparation of, a feed, such as functional feed, the enzyme or feed additive composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment, the enzyme or feed additive composition of the present invention is admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment, the term "feed component" encompasses a premix or premix constituents. Preferably, the feed may be a fodder, or a premix thereof, a compound feed, or a premix thereof.

A feed additive composition according to the present invention may be admixed with a compound feed, a compound feed component or to a premix of a compound feed or to a fodder, a fodder component, or a premix of a fodder.

Any feedstuff described herein may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grains (DDG) (particularly corn based Distillers Dried Grains (cDDG)), Distillers Dried Grains with Solubles (DDGS) (particularly corn based Distillers Dried Grains with Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

The term "fodder" as used herein means any food which is provided to an animal (rather than the animal having to forage for it themselves). Fodder encompasses plants that have been cut. Furthermore, fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

In one embodiment, the feedstuff comprises or consists of corn, DDGS (such as cDDGS), wheat, wheat bran or any combination thereof.

In one embodiment, the feed component may be corn, DDGS (e.g. cDDGS), wheat, wheat bran or a combination thereof. In one embodiment, the feedstuff comprises or consists of corn, DDGS (such as cDDGS) or a combination thereof.

A feedstuff described herein may contain at least 30%, at least 40%, at least 50% or at least 60% by weight corn and soybean meal or corn and full fat soy, or wheat meal or sunflower meal.

For example, a feedstuff may contain between about 5 to about 40% corn DDGS. For poultry, the feedstuff on average may contain between about 7 to 15% corn DDGS. For swine (pigs), the feedstuff may contain on average 5 to 40% corn DDGS. It may also contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff also may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grains (DDG), Distillers Dried Grains with Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton. In one aspect, the feedstuff as described herein comprises at least one high fibre material and/or at least one by-product of the at least one high fibre feed material selected from the group consisting of Distillers Dried Grains with Solubles (DDGS), particularly cDDGS, wet-cake, Distillers Dried Grains (DDG), particularly cDDG, wheat bran, and wheat for example. In one embodiment, the feedstuff of the present invention comprises at least one high fibre material and/or at least one by-product of the at least one high fibre feed material selected from the group consisting of Distillers Dried Grains with Solubles (DDGS), particularly cDDGS, wheat bran, and wheat for example.

The feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" as used herein encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

Animal feed can also include a fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

In still another aspect, animal feed encompasses bird food. Bird food includes food that is used both in birdfeeders and to feed pet birds. Typically, bird food comprises of a variety of seeds, but may also encompass suet (beef or mutton fat).

As used herein the term "contacted" refers to the indirect or direct application of a glycoside hydrolase as described herein (or composition comprising a glycoside hydrolase) to a product (e.g. the feed). Examples of application methods which may be used, include, but are not limited to, treating the product in a material comprising the feed additive composition, direct application by mixing the feed additive composition with the product, spraying the feed additive composition onto the product surface or dipping the product into a preparation of the feed additive composition. In one embodiment, the feed additive composition of the present invention is preferably admixed with the product (e.g.

feedstuff). Alternatively, the feed additive composition may be included in the emulsion or raw ingredients of a feedstuff. This allows the composition to impart a performance benefit.

The term "thermally stable" means that at least about 50%, 55%, 60%, 65%, 70%, 75%, 80%, 85%, 90%, 95%, 96%, 97% or 98% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

It is also possible that glycoside hydrolases (or an enzyme composition comprising such glycoside hydrolases as described herein) described herein can be homogenized to produce a powder.

In an alternative preferred embodiment, a glycoside hydrolase as described herein (or an enzyme composition comprising a glycoside hydrolase as described herein such) can be formulated to granules as described in WO2007/044968 (referred to as TPT granules) or WO1997/016076 or WO1992/012645 incorporated herein by reference. "TPT" means Thermo Protection Technology.

In another aspect, when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme. Preferably, the salt used for the salt coating has a water activity greater than 0.25 or constant humidity greater than 60% at 20° C. In some embodiments, the salt coating comprises $Na_2SO_4$.

A method of preparing a glycoside hydrolase as described herein (or an enzyme composition comprising a glycoside hydrolase as described herein) may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour. It will be understood that a glycoside hydrolase as described herein (or an enzyme composition comprising a glycoside hydrolase as described herein) are suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for pigs.

The feed additive composition and/or the feedstuff comprising the same may be used in any suitable form. The feed additive composition may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions may be mixed with feed or administered in the drinking water.

A feed additive composition, comprising admixing a glycoside hydrolase as taught herein with a feed acceptable carrier, diluent or excipient, and (optionally) packaging.

The feedstuff and/or feed additive composition may be combined with at least one mineral and/or at least one vitamin. The compositions thus derived may be referred to herein as a premix. The feedstuff may comprise at least 0.0001% by weight of the feed additive. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the feed additive.

Preferably, a food or feed additive composition may further comprise at least one physiologically acceptable carrier. The physiologically acceptable carrier is preferably selected from at least one of maltodextrin, limestone (calcium carbonate), cyclodextrin, wheat or a wheat component, sucrose, starch, $Na_2SO_4$, Talc, PVA and mixtures thereof. In a further embodiment, the food or feed additive may further comprise a metal ion chelator. The metal ion chelator may be selected from EDTA or citric acid.

In some embodiments, the food or feed additive composition comprises a glycoside hydrolase as described herein at a level of at least 0.0001 g/kg, 0.001 g/kg, at least 0.01 g/kg, at least 0.1 g/kg, at least 1 g/kg, at least 5 g/kg, at least 7.5 g/kg, at least 10.0 g/kg, at least 15.0 g/kg, at least 20.0 g/kg, at least 25.0 g/kg. In some embodiments, the food or feed additive comprises at a level such that when added to a food or feed material, the feed material comprises a glycoside hydrolase as described herein in a range of 1-500 mg/kg, 1-100 mg/kg, 2-50 mg/kg or 2-10 mg/kg. In some embodiments of the present invention the food or feed material comprises at least 100, 1000, 2000, 3000, 4000, 5000, 10000, 20000, 30000, 50000, 100000, 500000, 1000000 or 2000000 Units of glycoside hydrolase per kilogram feed or food material.

Ranges can include, but are not limited to, any combination of the lower and upper ranges discussed above.

Formulations comprising any of the glycoside hydrolases described herein and compositions described herein may be made in any suitable way to ensure that the formulation comprises active enzymes. Such formulations may be as a liquid, a dry powder or a granule. Preferably, the feed additive composition is in a solid form suitable for adding on or to a feed pellet.

Dry powder or granules may be prepared by means known to those skilled in the art, such as, high shear granulation, drum granulation, extrusion, spheronization, fluidized bed agglomeration, fluidized bed spray drying.

Glycoside hydrolases and compositions described herein may be coated, for example encapsulated. In one embodiment, the coating protects the enzymes from heat and may be considered a thermoprotectant. In one embodiment, the coating protects the enzyme from low pH. Eudragit® is one example of a coating material than can be used.

Feed additive composition described herein can be formulated to a dry powder or granules as described in WO2007/044968 (referred to as TPT granules) or WO1997/016076 or WO1992/012645 (each of which is incorporated herein by reference).

In one embodiment animal feed may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

Regarding the granule, at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

A granule may be produced using a steam-heated pelleting process which may be conducted between 85° C. and 95° C. for up to several minutes.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the enzyme(s) onto a carrier substrate, such as ground wheat for example.

In one embodiment, the feed additive composition may be formulated as a premix. By way of example only the premix may comprise one or more feed components, such as one or more minerals and/or one or more vitamins.

In some embodiments, a glycoside hydrolase will be in a physiologically acceptable carrier. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates. Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient. Once formulated, the compositions of the invention can be administered directly to the ruminant.

Non-limiting examples of compositions and methods disclosed herein include:

1. A method for increasing starch digestibility and glucose yield in a ruminant which comprises adding at least one alpha-1,4/1,6-glycoside hydrolase (GLCH) as a feed additive to feed for a ruminant wherein said hydrolase: (a) has at least 20% activity at pH less than or equal to 3 in the presence of pepsin as compared to activity of the hydrolase at pH 6 in the presence of pepsin, (b) said hydrolase is active in at least two of three digestive chambers of a ruminant comprising a rumen, an abomasum and a small intestine and (c) the hydrolase works with digestive enzymes present in the digestive chambers of the ruminant to increase starch digestibility and glucose yield.

2. The hydrolase of embodiment 1 wherein the at least one GLCH enzyme is capable of hydrolyzing raw starch under conditions comparable to those found in the rumen or abomasum.

3. The hydrolase of embodiment 1 wherein said hydrolase is selected from the group consisting of alpha-amylases, glucoamylases and alpha-glucosidases.

4. The hydrolase of embodiment 2 wherein said hydrolase is selected from the group consisting of alpha-amylases and glucoamylases.

5. The hydrolase of embodiment 3 or 4 wherein the alpha-amylases are members of the GH 13 family or are selected from the group consisting of alpha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC3.2.1.60); isoamylase (EC 3.2.1.68); glucodextranase (EC 3.2.1.70); maltohexaose-forming alpha-amylase (EC 3.2.1.98); maltotriose-forming alpha-amylase (EC 3.2.1.116); branching enzyme (EC 2.4.1.18); trehalose synthase (EC 5.4.99.16); 4-alpha-glucanotransferase (EC 2.4.1.25); maltopentaose-forming alpha-amylase (EC 3.2.1.-); amylosucrase (EC 2.4.1.4); sucrose phosphorylase (EC 2.4.1.7); malto-oligosyl-trehalose trehalohydrolase (EC 3.2.1.141); isomaltulose synthase (EC 5.4.99.11); malto-oligosyltrehalose synthase (EC 5.4.99.15); amylo-alpha-1,6-glucosidase (EC 3.2.1.33); and alpha-1,4-glucan: phosphate alpha-maltosyltransferase (EC 2.4.99.16).

6. The hydrolase of embodiment 3 or 4 wherein the glucosidases are members of the GH 13 or the GH31 family or are selected from the group consisting of alpha-glucosidase (EC 3.2.1.20); alpha-galactosidase (EC 3.2.1.22); alpha-mannosidase (EC 3.2.1.24); alpha-1,3-glucosidase (EC 3.2.1.84); sucrase-isomaltase (EC 3.2.1.48) (EC 3.2.1.10); alpha-xylosidase (EC 3.2.1.177); alpha-glucan lyase (EC 4.2.2.13); isomaltosyltransferase (EC 2.4.1.-); oligosaccharide alpha-1,4-glucosyltransferase (EC 2.4.1.161); sulfoquinovosidase (EC 3.2.1.-).

7. The hydrolase of embodiment 3 or 4 wherein the glucoamylases are members of the GH15 family or are selected from the group consisting glucoamylase (EC 3.2.1.3); glucodextranase. (EC 3.2.1.70); alpha-trehalase (EC 3.2.1.28); and dextran dextrinase (EC 2.4.1.2).

8. A method for increasing starch digestibility, increasing glucose yield, increase dry matter digestion and increase gas production during fermentation in a ruminant comprising adding to the feed an enzyme composition comprising (i) at least one GLCH enzyme as a feed additive for a ruminant wherein said enzyme: (a) has at least 20% activity at pH less than or equal to 3 in the presence of pepsin as compared to activity of the enzymes at pH 6 in the presence of pepsin, (b) said enzyme is active in at least two of three digestive chambers of a ruminant comprising a rumen, an abomasum and a small intestine and (c) the enzyme works with pancreatic amylase to increase glucose yield and (ii) at least one protease.

9. The enzyme composition of embodiment 8 wherein the at least one GLCH enzyme is capable of hydrolyzing raw starch.

10. The enzyme composition of embodiment 8 wherein said GLCH enzyme is selected from the group consisting of alpha-amylases, glucoamylases and alpha-glucosidases.

11. The enzyme composition of embodiment 9 wherein said enzyme is selected from the group consisting of alpha-amylases and glucoamylases.

12. The enzyme composition of embodiment 10 and 11 wherein the at least one GLCH enzyme is selected from the group consisting alpha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC3.2.1.60); isoamylase (EC 3.2.1.68); glucodextranase (EC 3.2.1.70); maltohexaose-forming alpha-amylase (EC 3.2.1.98); maltotriose-forming alpha-amylase (EC 3.2.1.116); branching enzyme (EC 2.4.1.18); trehalose synthase (EC 5.4.99.16); 4-alpha-glucanotransferase (EC 2.4.1.25); maltopentaose-forming alpha-amylase (EC 3.2.1.-); amylosucrase (EC 2.4.1.4); sucrose phosphorylase (EC 2.4.1.7); malto-oligosyltrehalose trehalohydrolase (EC 3.2.1.141); isomaltulose synthase (EC 5.4.99.11); malto-oligosyltrehalose synthase (EC 5.4.99.15); amylo-alpha-1,6-glucosidase (EC 3.2.1.33); and alpha-1,4-glucan: phosphate alpha-maltosyltransferase (EC 2.4.99.16).

13. The enzyme composition of embodiment 10 or 11 wherein the glucosidases are selected from the group consisting of alpha-glucosidase (EC 3.2.1.20); alpha-galactosidase (EC 3.2.1.22); alpha-mannosidase (EC 3.2.1.24); alpha-1,3-glucosidase (EC 3.2.1.84); sucrase-isomaltase (EC 3.2.1.48) (EC 3.2.1.10); alpha-xylosidase (EC 3.2.1.177); alpha-glucan lyase (EC 4.2.2.13); isomaltosyltransferase (EC 2.4.1.-); oligo-saccharide alpha-1,4-glucosyltransferase (EC 2.4.1.161); sulfoquinovosidase (EC 3.2.1.-).

14. The enzyme composition of embodiment 10 or 11 wherein the glucoamylases are selected from the GH15 glycosyl hydrolase family.

15. The enzyme composition of embodiment 8 wherein the protease is selected from the group consisting of an acid protease or a neutral metalloprotease.

16. The enzyme composition of embodiment 15 wherein the protease is a fungal aspartic protease or a bacterial neutral metalloprotease.

EXAMPLES

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY,* 2D ED., John Wiley and Sons, New York (1994), and Hale & Marham, *THE HARPER COLLINS DICTIONARY OF BIOLOGY,* Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

Materials Used in Subsequent Examples

The protein samples listed on Table 1 where used in subsequent examples. Table 1 shows the enzyme type, source organism (when known) and internal or commercial source for samples, and patent references for sequences.

TABLE 1

| List of enzymes components evaluated. | | | |
| --- | --- | --- | --- |
| Protein Name | Enzyme type | Organism Source | Reference |
| AkAA | alpha-amylase | Recombinant, *Aspergillus kawachii* source | U.S. Pat. No. 7,354,752 |
| AcAA | alpha-amylase | Recombinant, *Aspergillus clavatus* source | U.S. Pat. No. 8,945,889 |
| AtAA | alpha-amylase | Recombinant, *Aspergillus terreus* source | Patent US20150376668 |
| TrGA | glucoamylase | Recombinant, *T. reesei* source | U.S. Pat. No. 7,413,879 |
| CS4 | glucoamylase | Recombinant, variant | U.S. Pat. No. 8,058,033 |
| Brew1 | glucoamylase | Recombinant, variant | U.S. Pat. No. 8,809,023 |
| FvGA | glucoamylase | Recombinant, *Fusarium verticillioides* source | Patent WO2016100871 |
| AfuGA | glucoamylase | Recombinant, *Aspergillus fumigatus* source | Patent US20160115509 |
| AFP | protease | Recombinant, *T. reesei* source | U.S. Pat. No. 8,288,517 |
| Yeast maltase | alpha-glucosidase | Megazyme | Catalog # E-MALTS |
| TG L-2000 | alpha-glucosidase | Recombinant, *Aspergillus niger* source | US 2015/0240279 |
| Aclglu1 | alpha-glucosidase | Recombinant, *A. clavatus* source | US 20150240279 |
| Nfiglu1 | alpha-glucosidase | Recombinant, *Neosartorya fischeri* source | US 20150240279 |
| TauSec098 | alpha-glucosidase | *Rasamsonia composticola* | US 20150240279 |
| TauSec099 | alpha-glucosidase | *Rasamsonia composticola* | US 20150240279 |
| Porcine pepsin | protease | Sigma | Catalog # P7000 |
| Porcine pancreatin | Multiple enzymes | Sigma | Catalog # P7545 |
| P14L | neutral metalloendopeptidase (Thermolysin) | *Geobacillus caldoproteolyticus* | U.S. Pat. No. 8,114,656 |

TABLE 1-continued

| | List of enzymes components evaluated. | | |
|---|---|---|---|
| Protein Name | Enzyme type | Organism Source | Reference |
| P7L | neutral metalloendopeptidase (Bacillolysin) | *Bacillus amyloliquefaciens* | U.S. Pat. No. 8,574,884 |
| AnGA | glucoamylase | *Aspergillus niger*, Megazyme | Catalogue # E-AMGDF |

Example 2

Hydrolysis of Corn Flour by AkAA Amylase in the Presence of the Acidic Aspartic Protease Porcine Pepsin and *Trichoderma reesei* AFP The reaction mixture contained 1 mL corn flour slurry (20%, w/w, pH3.2), AkAA (209 mg/mL) 20 µL, porcine pepsin (Sigma, P7000, 10000 U/mL in water) 50 µL, AFP from *Trichoderma reesei* (5 mg/mL) 5 UL and 50 µL and water to a final volume of 1.07 mL. The reaction was performed at 40° C. for 5 h with shaking at 200 rpm. At the end of the reaction 30 µL of the reaction supernatant was mixed with 0.23 mL water and filtered through 0.22 µm membrane filter. The filtrate (40 µL) was subjected to HPLC analysis on an Aminex HPX-87N HPLC column (Bio-Rad) at a flow rate of 0.6 mL/min, at 78° C., over 15 min using water as eluent. Glucose and maltose peaks were detected using an inline RI (refractory index) detector, and the peak areas were integrated using Chromeleon software (Dionex) according to the manufacturer's instructions.

Activity of feed enzymes to ruminants should not be affected by pepsin if it is supposed to be functional in abomasum and small intestine.

FIG. 1 shows that neither pepsin nor AFP affected the release of glucose (G1) and maltose (G2) from corn flour at pH3.2 negatively. pH 3.2 is one of the pH values that can occur in abomasum especially after ingestion of feed (Constable et al., 2005. Effect of suckling cow's milk or milk replacer on abomasal luminal pH in dairy calves, J. Vet. Intern. Med. 19:97-102). In fact, addition of pepsin and AFP to the reaction mixture containing AkAA increased the release of G1 by 4 and 22%, respectively. Pepsin by itself brought little or no release of G1 and G2 from corn flour, whereas AFP by itself caused some release of G1 but no G2. AFP added to the reaction mixture containing AkAA not only increased the release of G1 but also increased the amount of G1 over G2, indicating AFP favoured more the release of glucose, a monomer (G1). It is G1 that can be directly absorbed by animals into the blood stream.

Under the conditions comparable to those found in the ruminal stomach and abomasum, it is believed that the two aspartic proteases may have made the corn starch granules more accessible to AkAA by hydrolyzing proteins surrounding the granules and proteins found inside the granules (Mu-Forster et al., 1996. Physical association of starch biosynthetic enzymes with starch granules of maize endosperm granule-associated forms of starch synthase I and starch branching enzyme II, Plant Physiol. 111:821-829; Mu-Forster et al., 1998. Surface localization of zein storage proteins in starch granules from maize endosperm, proteolytic removal by thermolysin and in vitro cross-linking of granule-associated polypeptides. Plant Physiol. 116:1563-1571). Pepsin is the major proteolytic enzyme produced in the stomach and abomasum. It digests proteins through the cleavage of interior peptide linkages with an optimum pH of 2-4. AFP is extracellular endopeptidase from *T. reesei* with pH optimum range of 3-4.5 (Table 1).

The corn used in Example 2 and other Examples, unless specified otherwise, consisted of 88.2% dry matter (DM), 9.3% crude protein (CP), 2.0% acid detergent fiber (ADF), 6.6% neutral detergent fiber treated with amylase (aNDF), 78.5% non-fibrous carbohydrates (NFC), 89.0% total digestible nutrients (TDN).

Example 3

Stability of AkAA Amylase in the Presence of Rumen Fluid

For an animal feed enzyme additive to be effective in ruminants, it is important that the enzyme have considerable stability in rumen fluid and under ruminal conditions. Data in Table 2 show that AkAA is stable in the presence of cell-free rumen fluid incubated at 40° C. for 4.5 h, as the release of glucose and maltose was not significantly affected by increasing amounts of rumen fluid.

The AkAA used had a total protein concentration of 209 mg/mL, rice starch granules (Sigma S7260) were prepared in water at 8% (w/w) slurry with pH adjusted to 3.2. The pH became pH 5.3 after mixing with the pre-incubation mixture. The cell-free rumen fluid had a pH of 6.1 collected from dairy cow fed a mixed ration of grass (41.66%), whole barley (14.79%), maize (16.78%), dried sugar-beet pulp and sugar beet residue cake (3.02%), ground barley (6.66%), rape seed meal (4.88%), soybean meal (4.46%), Komix (vitamin and mineral mix, 0.2%), Roed Suplex Caps (vitamin mix 0.05%), Suplex E-5000 (vitamin E and selenium, 0.03%), chalk (0.07%), salt (0.06%), and water (7.33%). The rumen fluid was offered from Department of Animal Science, Aarhus University (Blichers Alle 20, DK-8830 Tjele, Denmark). The sugar released from the reaction was analyzed on HPLC with Aminex HPX-87N HPLC column from Bio-Rad as Example 2.

TABLE 2

| Stability of AkAA in rumen fluid at 40° C. for 4.5 h. | | | | | | | | | | |
|---|---|---|---|---|---|---|---|---|---|---|
| | Treatment No. (n = 3) | | | | | | | | | |
| | 1 | 2 | 3 | 4 | 5 | 6 | 7 | 8 | 9 | 10 |
| Rumen fluid, µL | 0 | 0 | 90 | 90 | 140 | 140 | 190 | 190 | 240 | 240 |
| AkAA, µL | 0 | 10 | 0 | 10 | 0 | 10 | 0 | 10 | 0 | 10 |
| Heat treated rumen fluid, µL | 240 | 240 | 150 | 150 | 100 | 100 | 50 | 50 | 0 | 0 |

TABLE 2-continued

| Stability of AkAA in rumen fluid at 40° C. for 4.5 h. | | | | | | | | | |
| --- | --- | --- | --- | --- | --- | --- | --- | --- | --- |
| Treatment No. (n = 3) | | | | | | | | | |
| 1 | 2 | 3 | 4 | 5 | 6 | 7 | 8 | 9 | 10 |
| Pre-incubation at 40° C. for 4.5 h with shaking at 200 rpm and then add additional AkAA and the substrate rice starch to start the catalytic reaction | | | | | | | | | |

| | 1 | 2 | 3 | 4 | 5 | 6 | 7 | 8 | 9 | 10 |
| --- | --- | --- | --- | --- | --- | --- | --- | --- | --- | --- |
| AkAA, µL | 10 | 0 | 10 | 0 | 10 | 0 | 10 | 0 | 10 | 0 |
| Rice starch slurry, mL | 1.0 | 1.0 | 1.0 | 1.0 | 1.0 | 1.0 | 1.0 | 1.0 | 1.0 | 1.0 |
| Enzyme reaction at 40° C. for 3 h with shaking at 200 rpm Supernatant obtained at the end of the reaction was diluted 4 times with water and 40 µL was injected for HPLC analysis of glucose (G1) and maltose (G2) released | | | | | | | | | | |
| G1 peak area | 5.78 | 6.25 | 5.75 | 5.48 | 6.86 | 7.15 | 7.43 | 6.62 | 6.70 | 6.28 |
| G2 peak area | 4.33 | 4.08 | 4.18 | 4.07 | 3.96 | 3.89 | 3.89 | 3.74 | 4.06 | 3.83 |
| G1 + G2 peak area | 10.11 | 10.32 | 9.93 | 9.56 | 10.82 | 11.04 | 11.32 | 10.36 | 10.76 | 10.11 |
| Percentage of Treatment No. 1 | 100 | 102 | 98 | 95 | 107 | 109 | 112 | 102 | 106 | 100 |

Example 4

Stability of AkAA to Pancreatin and Effect of AkAA with Pancreatin in Increasing Glucose Yield and Reducing Maltotriose Yield The reaction mixture contained porcine pancreatin (Sigma P7545, 25 mg/ml made in 0.1% NaCl) at 0, 5, 10 and 20 µL, AkAA (209 mg/mL) 20 µL, 0.1 M Mes (pH6.7) 60 µL having 5 mM $CaCl_2$), Tween 80 (0.01% w/v). NaCl solution at 0.1% was added to a final reaction volume of 0.12 mL. The reaction mixture was incubated at 40° C. for 3 h and then the substrate 1.5 mL corn flour slurry (10% w/w) was added and further incubated at 40° C. for 13 h. The supernatant obtained was diluted 8.33-fold and 40 µL was analyzed on HPLC for glucose, maltose and maltotriose using RI detector as described in Example 2.

FIG. 2 shows that AkAA was active under conditions simulating those of the ruminal small intestine. It showed both additional and complementary effect with the 3 doses of porcine pancreatin (Pan) tested. The inclusion of AKAA with Pan increased glucose and maltose production and decreased maltoriose formation/accumulation, which is nutritionally advantageous as glucose can be directly absorbed while maltose can be hydrolysed by intestinal mucosal alpha-glucosidase (maltase) (Nichols et al., 1998. Human small intestinal maltase-glucoamylase cDNA cloning, homology to sucrase-isomaltase, J. Biol. Chem. 273: 3076-3081). Pancreatin is the major digestive enzyme cocktail for animals, especially, monogastrics and ruminants. It contains enzymatic components such as trypsin, amylase and lipase, ribonuclease, and protease, produced by the exocrine cells of the porcine pancreas. Thus, pancreatin is a combination of enzymes allowing it to hydrolyse proteins, starch and fats.

Example 5

Activity of AtAA Amylase on Corn Flour in the Presence of Pepsin and Pancreatin

For the pepsin reaction, the reaction mixture had 0.1 mL corn starch slurry at 10% (w/w) (Sigma S4126) prepared in 60 mM glycine-HCl (pH2.5), 10 µL pepsin (Sigma P7000, 10000 U/mL in water), and 0.6 µL (16.76 mg/mL) AtAA amylase. The reaction was carried at 40° C. for 3 h. The samples were centrifuged. The supernatant was diluted, filtered and analysed on HPLC using RI detector for sugar analysis as described in Example 2. The pancreatin reaction was the same as the pepsin reaction except the corn starch slurry was prepared in 0.1 M Mes (pH 6.7) and 5 µL of 25 mg/mL porcine pancreatin (Pan) (Sigma P7545, dissolved in 0.1% NaCl) was added.

FIG. 3 shows that *Aspergillus terreus* alpha-amylase AtAA (AtAmy1) was active when tested in the presence of either pepsin at pH2.5 or pancreatin at pH6.7. Furthermore, AtAA and pancreatin showed a complementary effect in converting all maltotriose basically to glucose that can be directly absorbed by the animals.

Example 6

Corn Starch Hydrolysis by AkAA and AcAA Amylases in the Presence of Rumen Fluid

Cell-free rumen fluid, 240 µL was mixed with 10 µL of enzyme samples: AkAA (209 mg/mL), AcAA (172 mg/mL), AkAA with *Trichoderma reesei* GA (TrGA) and *Trichoderma reesei* AFP (223 mg/mL), or AcAA with TrGA variant CS4 and AFP (125 mg/mL) (Table 1) and incubated at 40° C. for 4 h followed by the addition of 250 µL of corn starch (Sigma S4126) slurry dissolved in 0.1 M acetate containing 5 mM $CaCl_2$) (pH4.5) and further incubated for 30 min. At the end of the reaction, the reaction samples were filtered and the supernatants were analysed for detection of total reducing sugars by using alkaline 3,5-dinitrosalicylic acid (DNS) reagent according to Yu et al., (Yu et al, 1997. Methods for the assay of 1,5-anhydro-D-fructose and alpha-1,4-glucan lyase. Carbohydr. Res. 305:73-82) with minor modification. That is, diluted reaction samples 10 µL were transferred to a 96 well PCR plate containing 120 µL of the DNS reagent. The plate was incubated at 95° C. for 5 min followed by 5 min cooling to 20° C. and then 100 µL of these mixtures were transferred to a new 96 well plate that was used to measure the optical density at 550 nm in a spectrophotometer.

FIG. 4 shows very minor reduction on corn hydrolysis activity for all the 4 enzyme samples tested after incubation in rumen fluid. The presence of *Trichoderma reesei* GA and its variant (CS4) and *Trichoderma reesei* AFP enzymes had a beneficial effect on the total hydrolysis of the substrate catalysed by both AkAA and AcAA amylase samples. Both enzyme mixtures of amylase/glucoamylase/protease were prepared in a 29:70:1 ratio of total protein. As shown in FIG. 4, the amylases AkAA, AcAA and their mixture with glucoamylases TrGA and CS4 and the aspartic protease AFP lost less than 13% of their total activity after 4 h pre-incubation in rumen fluid at 40° C. followed by 30 min incubation with corn starch at 40° C. pH 4.5 (when compared to untreated mixtures).

These results under simulated rumen conditions indicate that these two amylases and their mixtures with glucoamylases and aspartic peptidase could survive in the digestive tract of a ruminant.

Example 7

Activity of AkAA and AcAA Amylases in the Presence Pepsin Under Different pH Conditions The reaction mixture contained 1.0 mL corn flour slurry (20% w/w) prepared in 0.1 M glycine-HCl (pH 3.2), 0.1 M acetate (pH 4.1, 4.7) or 0.1 M Mes (pH 6.0) all having 5 mM $CaCl_2$), 25 µL of AkAA (209 mg/mL) or AcAA (172 mg/mL), 25 µL pepsin (Sigma P7000, 10000 U/mL in water). The reaction was carried at 40° C. for 2 h. At the end of the reaction, the supernatant obtained by centrifugation was filtered through 0.45 µm filter and diluted by 20 times. The diluted samples were assayed for total reducing sugar as detailed in Example 6.

FIG. 5 shows corn flour hydrolysis by AkAA and AcAA samples incubated at pH 3.2, 4.1, 4.7 and 6.0 in the absence or presence of pepsin. The amylase activity measured as the release of total reducing sugar by AkAA and AcAA was not significantly affected in the presence of pepsin compared to in the absence of pepsin. It further indicates that these two amylases sharing 70% identity are active under conditions comparable to what would be found in the digestive tract of a ruminant: e.g., one of the abomasum acidity conditions (pH 3.2), upper small intestine conditions (pH4.1-4.7) and conditions comparable to those found in the small intestine and rumen (both at pH6.0 or near pH6.0). Thus, AkAA and AcAA amylases appear more active at rumen-relevant pH that other amylases currently in use as monogastric feed additives, such as alpha-amylases from *Bacillus amyloliq-uefaciens, B. licheniformis, B. subtilis, Aspergillus niger* and *A. oryzae* (Monteiro de Souza et al., Application of microbial alpha-amylase in industry—a review. Brazilian Journal of Microbiology (2010) 41:850-861).

Example 8

Activity of Endo-/Exo-Glucan Hydrolases and Endo Protease Mixtures in the Presence of Pancreatin The reaction mixture contained 1.0 mL corn flour slurry (20% w/w, in 0.1 M Mes, 5 mM $CaCl_2$) pH 6.0), 25 µL of the enzyme cocktail of AkAA+TrGA+AFP (223 mg/mL) or AcAA+CS4+AFP (125 mg/mL), 25 µL porcine pancreatin (Sigma P7545, 25 mg/mL made in 0.1% NaCl). The reaction was carried at 40° C. for 2 h. At the end of the reaction, the supernatant obtained by centrifugation was filtered through 0.45 µm filter and diluted by 20 times. The diluted samples were assayed for total reducing sugar as detailed in Example 6. FIG. 6 shows that after 2 h incubation with corn flour (20% w/w) at 40° C. pH 6.0 in the presence of pancreatin, the enzyme mixture of AkAA+TrGA+AFP and the enzyme mixture of AcAA+CS4+AFP increased the reducing sugar production by 4.2 and 3.8-fold, respectively. This study shows that the AkAA+TrGA+AFP and AcAA+CS4+AFP mixture survived in the passage through the rumen and abomasum may work synergistically with pancreatin enzymes to promote sugar release.

Like AkAA (Example 4), AcAA was also found to work synergistically with pancreatin. Table 3 shows that if AcAA is dosed together with pancreatin, the generation of reducing power (DNS value) is 1.6-fold of the sum of reducing power generated individually by the two enzymes at pH6.0 and the corresponding value at pH6.7 is 1.25-fold.

The reaction mixture contained 1 mL 20% w/v corn starch slurry in 0.1 M Mes (pH 6.0 and 6.7) having 5 mM $CaCl_2$), with and without 25 µL of porcine pancreatin (2.5% w/v) and 25 µL AcAA (17.2 mg/mL) at 40° C. for 2 h. Reducing sugar generated was assayed as in Example 6.

TABLE 3

| The synergy effect of AcAA with pancreatin at pH 6.0 and 6.7 | | |
|---|---|---|
| Treatment | pH 6.0 | pH 6.7 |
| Control (no amylase or pancreatin) | 1.16 | 1.00 |
| Pancreatin only minus control | 1.96 | 1.80 |
| AcAA only minus control | 1.24 | 1.06 |
| AcAA dosed together with Pancreatin minus control | 5.12 | 3.57 |

Example 9

Reducing Sugar Releasing Activity of the Endo-, Exo-Glucan Hydrolases and Endo Protease Mixtures AFP in the Presence of Pepsin at pH2.5 Relative to pH 6.0

Table 4 shows that the activity of the mixture of AkAA, AcAA, TrGA, CS4 and AFP in the absence and presence of pepsin at pH2.5 relative to pH 6.0. It can be seen that the activity at pH2.5 is over 20% vs pH6.0 for both enzyme cocktails under the experimental conditions. It would be advantageous for enzymes in the enzyme cocktails to be both stable and active under conditions comparable to those found in the stomach or abomasum of a ruminant where lower pH prevails.

The reaction mixture contained 1.0 mL corn flour slurry (10%, w/w) in 0.1 M Glycine-HCl (pH2.5) having 5 mM $CaCl_2$) or in 0.1 M Mes-NaOH (pH6.0) having 5 mM $CaCl_2$), 25 µL enzyme cocktail of AkAA+TrGA+AFP (223 mg/mL) or AcAA+CS4+AFP (125 mg/mL), and 25 µL pepsin (10000 U/mL). The reaction was carried out at 40° C. for 2 h with shaking at 300 rpm. At the end of the reaction, the substrate was separated from the enzyme and the products by centrifugation at 3500 rpm for 5 min in a 0.45 µm filter 96 well filter plate. The filtrate was diluted 2 times and assayed for reducing sugar value as described in Example 6.

TABLE 4

Reducing sugar releasing activity of the endo-, exo-glucan hydrolases and endo protease mixture of AkAA, AcAA, TrGA, CS4 and AFP in the presence and absence of pepsin at pH 2.5 relative to pH 6.0. Activity at pH 6.0 is regarded as 100%.

| Reaction pH | Control | Control + Pepsin | AkAA + TrGA + AFP | AkAA + TrGA + AFP + Pepsin | AcAA + CS4 + AFP | AcAA + CS4 + AFP + Pepsin |
|---|---|---|---|---|---|---|
| pH 2.5 | 0.375 | 0.368 | 0.569 | 0.610 | 0.424 | 0.450 |
| pH 6.0 | 0.390 | 0.395 | 0.547 | 0.587 | 0.624 | 0.612 |
| pH 2.5 vs pH 6.0, % | | | 123 | 126 | 21 | 38 |

Example 10

Corn Starch Hydrolysis by Glucoamylase Under Small Intestine Digestive Conditions in the Presence of Pancreatin The reaction mixture contained 0.5 mL corn starch slurry (Sigma S4126) or corn flour slurry (10% w/v) in 0.1 M Mes (pH6.0), 50 μL pancreatin (final concentration in the reaction mixture 0.25%) and the glucoamylase at 400 ppm at a final volume 0.56 mL. The reaction was carried out at 40° C. for 1 h with shaking at 300 rpm. At the end of the reaction, the supernatant was obtained by centrifugal separation from the starch granules using bench top centrifuge and assayed for total reducing sugar by the DNS reagent method described in Example 6, namely 10 μL of the supernatant or diluted supernatant was mixed with 100 μL DNS reagent in a 96 well PCR plate. The PCR plate was then incubated at 95° C. for 5 min followed by 5 min cooling to 20° C. The reaction mixture 90 μL was transferred to a 96 well reading plate and absorbance at 550 nm was measured as the DNS value.

FIG. 7, with corn starch as substrate, and FIG. 8, with corn flour as substrate, show that all the five glucoamylases of CS4, TrGA, Brew1, AfuGA and FvGA (for details see Table 1) worked synergistically with pancreatin in producing reducing sugars as indicated in DNS values. Glucoamylases (GAs) (1,4-alpha-D-glucan glucohydrolase (EC 3.2.1.3) catalyze hydrolysis of alpha-1,4 and alpha-1,6-glucosidic linkages to release beta-D-glucose from the non-reducing ends of starch and related poly- and oligosaccharides (Sauer et al. 2000. Glucoamylase: structure/function relationships, and protein engineering, Biochim. Biophys. Acta, 1543:275-293). Thus, in contrast to certain types of alpha-glucosidases, GA is also capable of hydrolyzing raw starch and alpha-1,4, and alpha-1,6-glucosidic linkages found in alpha-glucans and its oligomers.

FIGS. 7 and 8 shows that the porcine pancreatin and all five GAs had certain capabilities to hydrolyze corn starch granules with the highest activity observed for FvGA at pH6.0 and 40° C. A significant synergy was observed when the reaction mixture contained both the GAs and the porcine pancreatin. It is believed that such synergism may be due not only to the pancreatic alpha-amylase present in the pancreatin product purchased from Sigma, but also possibly due to the proteases present as well in this pancreatin product which can interact with any protein that may be present on the surface of the corn starch granules as well as inside the granule.

This example shows that glucoamylases can work synergistically with pancreatic digestive enzymes in generating glucose from the corn with chemical composition given in (see Example 2. The five GAs used in this experiment and the three alpha amylases AkAA, AcAA and AtAA used in Examples 2-9 above all have carbohydrate binding modules belonging to family 20 (CBM20) (Christiansen et al., 2009. The carbohydrate-binding module family 20—diversity, structure, and function, FEBS Journal, 276:5006-5029; Janeceka et al., 2011. Structural and evolutionary aspects of two families of non-catalytic domains present in starch and glycogen binding proteins from microbes, plants and animals. Enzyme and Microbial Technology, 49:429-440). These enzymes may have an additional carbohydrate binding site beside the carbohydrate binding module (Sorimachi et al., 1997. Solution structure of the granular starch binding domain of Aspergillus niger glucoamylase bound to beta-cyclodextrin, Structure, 5:647-661). These carbohydrate binding modules and carbohydrate binding sites may be necessary for activity on starch granules and maltosaccharides and, thus, contribute to the synergistic effect when combined with pancreatin.

Example 11

Corn Starch Hydrolysis by Glucoamylase Under Ruminal Conditions

Table 5 shows that remaining activity for the five glucoamylases is at least 80% after 4 h incubation in ruminal fluid in the absence of starch substrate, except for AfuGA which has 65% activity left. As a feed enzyme for ruminants, it is necessary to have considerable stability in ruminal fluid at 40° C. for 4 h.

Thus, these enzymes show usefulness as feed enzymes for ruminants since they were stable and retained activity in ruminal fluid at 40° C. for 4 h.

The pre-incubation mixture contained 0.25 mL cell-free ruminal fluid, 5 μL each of the 5 glucoamylases at 400 ppm. The pre-incubation was at 40° C. for 4 h with shaking at 300 rpm in a 48 well plate. For control the pre-incubation time was zero. After the pre-incubation 0.25 mL corn starch (Sigma S4126) slurry (10% w/v) in 0.1 M Mes (pH6.0) were added and reacted for 30 min at 40° C. with shaking. The supernatant was obtained by centrifugal separation from the starch granules using bench top centrifuge and assayed for total reducing sugar by the DNS method as described in Example 10.

TABLE 5

Stability of five glucoamylases in the presence of ruminal fluid at 40° C. for 4 h.

| Glucoamylases | Remaining Activity on corn starch (%) |
|---|---|
| CS4 | 81 |
| TrGA | 98 |
| Brew1 | 86 |

TABLE 5-continued

| Stability of five glucoamylases in the presence of ruminal fluid at 40° C. for 4 h. | |
| --- | --- |
| Glucoamylases | Remaining Activity on corn starch (%) |
| AfuGA | 65 |
| FvGA | 80 |

Example 12

Activity of Five Glucoamylases at pH 2.5 Relative to pH6.0 in the Presence of Pepsin It would be advantageous for enzymes to be both stable and active under conditions simulating those found in the ruminal stomach or ruminal abomasum where lower pH prevails. The activity at pH2.5 should be considerably high enough to have significance in digestibility in this low pH digestion chamber relative to the activity in the rumen and small intestine with a pH of around 6 based on starchy diet. Table 6 shows that all five glucoamylases have more than 20% activity at pH2.5 compared to their activity at pH6.0. Thus, a balanced activity in rumen, abomasum and small intestine will increase the opportunities to digest starchy nutrients.

The reaction mixture contained in 48 well microplate 0.5 mL corn flour slurry (10% w/v) prepared in Glycine-HCl (60 mM pH2.5) or in Mes-NaOH (100 mM, pH6.0), 50 μL porcine pepsin (final concentration 1000 U/mL), and 5 μL glucoamylase (final concentration, 400 ppm). The reaction was carried out at 40° C. for 60 min. Released reducing sugar was analyzed by the DNS reagent as described in Example 10. Activity at pH6.0 is used as 100%.

TABLE 6

| Activity ratio of the five glucoamylases at pH 2.5 and pH 6.0. Activity at pH 6.0 for each enzyme is reported as 100%. | | | |
| --- | --- | --- | --- |
| Glucoamylases | pH 2.5 | pH 6.0 | pH 2.5 vs pH 6.0, % |
| CS4 | 0.497 | 0.793 | 63 |
| TrGA | 0.498 | 0.778 | 64 |
| Brew1 | 0.491 | 0.578 | 85 |
| AfuGA | 0.663 | 0.715 | 93 |
| FvGA | 0.220 | 0.692 | 32 |

Example 13

Glucose Release from Corn Starch by Yeast Alpha-Glucosidase in the Presence of Pancreatin Under Small Intestine Simulating Conditions The reaction mixture contained: 0.5 mL corn starch (Sigma S4126) slurry (10% w/v) suspended in 0.1 M Mes (pH 6.0) containing 5 mM $CaCl_2$, 0, 10, 20 or 35 μL yeast alpha-glucosidase (which can also be referred to as maltase purchased from Megazyme, E-MALTS, 1000 U/mL), 0 to 25 μL porcine pancreatin (2.5% w/v in 1% NaCl, purchased from Sigma cat. NO. P7545), and 0 to 60 μL water, in a total volume of 0.56 mL. The reaction mixtures were incubated in a shaking incubator at 40° C. for 60 min in 48 well plate. The plate was centrifuged at 3500 rpm for 10 min using a bench top centrifuge to separate undigested starch granules. The supernatant obtained was transferred to a 96 well plate for glucose assay using the glucose assay kit based on glucose oxidase/peroxidase (GOPOD).

For the GOPOD glucose assay, 8 μL the supernatant was transferred to 96 well reading plate having 240 μL GOPOD reagent from Megazyme (K-GLUC 09/14). The plate was incubated at 50° C. for 20 min and absorbance at 510 nm was read according to instructions from Megazyme.

It is well known that pancreatin product (Sigma P7545) contains pancreatic alpha-amylase, lipase, ribonuclease and several proteases including trypsin, chymotrypsin, elastase. The hydrolytic products of dietary starch by porcine and bovine alpha-amylase are mainly maltose (Banks et al., 1976. The action pattern of bovine pancreatic alpha-amylase. Intl J. Biochem., 7:107-110). It is known that animals, including monogastric animals and ruminants, hydrolyze maltose using a small intestinal membrane bound enzyme (Nichols et al., 1998. Human Small Intestinal Maltase-glucoamylase cDNA Cloning, homology to sucrase-iso-maltase, J. Biol. Chem. 273:3076-3081). Freely moving enzyme has greater catalytic efficacy than a membrane-bound (immobilized) enzyme.

FIG. 9 shows that, without pancreatin, yeast alpha-glucosidase dosed from 0, 10, 20, to 35 μL was not able to increase the glucose release from corn starch granules.

However, in the presence of 2.5 μL pancreatin, glucose was released, and the addition of 10 μL alpha-glucosidase doubled the amount of glucose released. Glucose yield increased further as the dose of alpha-glucosidase was increased. This indicates that the yeast alpha-glucosidase worked synergistically with the enzymes present in pancreatin to release glucose from corn starch. It is believed that the proteases present in pancreatin may promote to some extent this synergism since protease can hydrolyze proteins present on the surface of the starch granules as well as proteins residing inside the granule. These proteins on and inside the starch granules may affect starch digestion negatively (McAllister et al., 1993. Effect of the protein matrix on the digestion of cereal grains by ruminal microorganisms. *J. Anim. Sci.* 71:205-212).

The alpha-glucosidase used in Example 13 is a highly purified form from *Saccharomyces cerevisiae* purchased from Megazyme International Ireland (EC 3.2.1.20, CAZy Family: GH13, Protein database entries: P53341, P38158, CAS: 9001-42-7). This example shows that free microbial alpha-glucosidase has good synergism with pancreatic digestive enzymes. This yeast alpha-glucosidase was found, however, unstable and inactive under conditions comparable to those found in the ruminal stomach and ruminal abomasum. It is believed that further efforts such as coating this yeast alpha-glucosidase or protein engineering may be needed to make it stable under such low pH in the presence of pepsin so that it will be able to function in the ruminal small intestine.

Example 14

Glucose Release from Corn Starch by Fungal Alpha-Glucosidases in Presence of Pancreatin Under Conditions Mimicking Those of the Small Intestine Three fungal alpha-glucosidases: TG L-2000, Aclglu1 and Nfiglu1 (Table 1) were examined for stability and activity in the presence of pepsin, pancreatin and rumen fluid (Tables 7.1, 7.2 and 7.3 below). Tables 7.1-7.3 show that all the three alpha-glucosidases worked synergistically with pancreatin in increasing glucose release from corn starch.

The synergy study with pancreatin was conducted as follows: 0.5 mL corn starch (Sigma S4126) slurry (10% w/v)

in 0.1 M Mes (pH6.0) having 5 mM $CaCl_2$) was incubated with 0 or 2.5 μL alpha-glucosidase TG L-2000 (3.1 mg/mL) and 0 or 2.5 μL porcine pancreatin (Sigma P7545, 2.5% w/v in 1% NaCl). The reaction was carried out at 40° C. for 1 h. The reaction mixture was then filtered through 0.22 μm filter. Released glucose in the filtrate was assayed using Megazyme glucose assay kit (GOPOD) (K-GLUC 09/14) (as described in Example 13 above) and was performed as follows: 8 μL of filtrate was mixed with 0.24 mL GOPOD reagent in a 96 well plate and read at 510 nm after incubation at 50° C. for 20 min. The OD units measured at 510 nm were used as a quantification of glucose release.

The synergy study with pepsin and pancreatin (Pan) was conducted as follows: the pre-incubation mixture contained 0.1 mL glycine-HCl (pH3.0), 5 mM CaCl2, 25 μL porcine pepsin (Sigma P7000, 5000 U/mL) and 2.5 μL TG L-2000. This mixture was incubated at 4° C. for 2 h. At the end of the incubation, 0.5 mL corn starch slurry (10%, w/v) in 0.1 M Mes (pH6.0) and 2.5 μL pancreatin (2.5%) were added and further incubated at 40° C. for 1 h. Assay of released glucose was performed as described above with respect to the pancreatin study using the Megazyme glucose assay kit.

The stability and interaction with rumen starch hydrolase study was done as follows: 2.5 μL alpha-glucosidase TG L-2000 with 0.24 mL cell-free rumen fluid and incubating at 40° C. for 4 h. At the end of the incubation, 0.25 mL corn starch (10% w/v) in 0.1 M acetate (pH4.5) was added and further incubated at 40° C. for 30 min. Released glucose was assayed using the Megazyme glucose assay kit as described above for the pancreatin study.

sum of the individual releases by Aclglu1 and pancreatin or Nfiglu1 and pancreatin, respectively.

Pepsin stability of the three alpha-glucosidases was tested at pH3.0 in the presence of pepsin (Table 7.1). It is evident that the combination of 2.5 μL alpha-glucosidase TG L-2000 and pancreatin increased glucose release by 7.3-fold even after pre-incubation with pepsin in the absence substrate at pH3.0 and 40° C. for 2 h (Table 7.1). For alpha-glucosidases, Aclglu1 and Nfiglu1, tested under the same conditions, the increase in glucose release by the combination was 4.1-fold (Table 7.2) and 6.9-fold (Table 7.3). All three alpha-glucosidases showed pepsin stability because, despite pre-incubation with pepsin, all of them still showed a synergistic effect when combined with pancreatin in the assay mixture.

Similarly, synergy and stability of the three alpha-glucosidases in rumen fluid (Table 7.1-7.3) was evaluated. Table 7.1 shows that for alpha-glucosidase TG L-2000, added to rumen fluid, glucose release increased 2.0-fold compared to the sum of glucose released individually by alpha-glucosidase TG L-2000 and by rumen fluid; and with pre-incubation in rumen fluid, the presence of TG L-2000 glucose release also increased 2.0-fold compared to the release in the absence of the alpha-glucosidase (Table 7.1), meaning that alpha-glucosidase TG L-2000 is stable in rumen fluid. For the alpha-glucosidase Aclglu1 and Nfiglu1, their presence resulted in increased glucose release by 2.0 and 2.8-fold, respectively for "no pre-incubation and pre-incubation treatments" (Table 7.2-7.3) with rumen fluid.

TABLE 7.1

Synergy effect of alpha-glucosidase TG L-2000 from *Aspergillus niger* with pancreatin (Pan), amylolytic activity in rumen fluid, and tolerance in the presence of pepsin in the release of glucose (G1) from corn starch. The number of repetitions (n) was 2-4.

| | No Pan | With Pan | With Pan | Pepsin + Pan incubation at 40° C. for 2 h | Pepsin + Pan incubation at 40° C. for 2 h | No pre-incubation with rumen fluid | No pre-incubation with rumen fluid | Pre-incubated with rumen fluid at 40° C. for 4 h | Pre-incubated with rumen fluid at 40° C. for 4 h |
|---|---|---|---|---|---|---|---|---|---|
| TG L-2000 | + | − | + | − | + | − | + | − | + |
| OD510 nm | 0.16 | 0.086 | 1.29 | 1.175 | 8.544 | 0.494 | 0.885 | 0.982 | 1.822 |
| Standard deviation | 0.005 | 0.001 | 0.014 | 0.145 | 0.276 | 0.199 | 0.05 | 0.117 | 0.11 |
| Fold increase in G1 release due to addition of TG L-2000 | | | 5.2 | | 7.3 | | 2.0 | | 2.0 |
| n | 2 | 4 | 2 | 4 | 2 | 4 | 2 | 4 | 2 |

Alpha-glucosidase and porcine pancreatin used individually produced a limited release of glucose from corn starch (Table 7.1). The combination of alpha-glucosidase TG L-2000 and pancreatin released a glucose amount 5.2 times higher than the sum of the individual glucose release by each of the two enzyme preparations (Table 7.1). Similarly, when Aclglu1 and Nfiglu1 were combined with pancreatin under the same conditions, the increase in glucose release was 8.3-fold (Table 7.2) and 7.8-fold (Table 7.3) compared to the Table 7.2. Synergy effect of alpha-glucosidase from *Aspergillus clavatus* (Aclglu1) with pancreatin (Pan), amylolytic activity in rumen fluid and tolerance in the presence of pepsin in the release of glucose (G1) from corn starch.

The reaction and assay conditions were the same as for Table 7.1 except that 0 or 50 μg alpha-glucosidase Aclglu1 (Table 1) from *A. clavatus* was used. The number of repetitions (n) was 2-4.

| | No Pan | With Pan | With Pan | Pepsin + Pan incubation at 40° C. for 2 h | Pepsin + Pan incubation at 40° C. for 2 h | No pre-incubation with rumen fluid | No pre-incubation with rumen fluid | Pre-incubated with rumen fluid at 40° C. for 4 h | Pre-incubated with rumen fluid at 40° C. for 4 h |
|---|---|---|---|---|---|---|---|---|---|
| Aclglu1 | + | − | + | − | + | − | + | − | + |
| OD510 nm | 0.06 | 0.086 | 1.22 | 1.175 | 4.845 | 0.494 | 0.75 | 0.982 | 2.05 |
| Standard deviation | 0.003 | 0.001 | 0.013 | 0.145 | 0.52 | 0.199 | 0.03 | 0.117 | 0.08 |
| Fold increase in G1 release due to addition of Aclglu1 | | | 8.3 | | 4.1 | | 2.0 | | 2.8 |
| n | 2 | 4 | 2 | 4 | 2 | 4 | 2 | 4 | 2 |

Table 7.3. Synergy effect of alpha-glucosidase from Neosartorya *fischeri* (Nfiglu1) with pancreatin (Pan), amylolytic activity in rumen fluid and tolerance in the presence of pepsin in the release of glucose (G1) from corn starch.

The reaction and assay conditions were the same as described above with respect to Table 7.1 except that 0 or 50 µg alpha-glucosidase Nfiglu1 from *N. fischeri* was used. The number of repetitions (n) were 2-4.

| | No Pan | With Pan | With Pan | Pepsin + Pan incubation at 40° C. for 2 h | Pepsin + Pan incubation at 40° C. for 2 h | No pre-incubation with rumen fluid | No pre-incubation with rumen fluid | Pre-incubated with rumen fluid at 40° C. for 4 h | Pre-incubated with rumen fluid at 40° C. for 4 h |
|---|---|---|---|---|---|---|---|---|---|
| Nfiglu1 | + | − | + | − | + | − | + | − | + |
| OD510 nm | 0.08 | 0.086 | 1.29 | 1.175 | 8.12 | 0.494 | 0.73 | 0.982 | 2.06 |
| Standard deviation | 0.002 | 0.001 | 0.077 | 0.145 | 0.13 | 0.199 | 0.01 | 0.117 | 0.00 |
| Fold increase in G1 release due to addition of Nfiglu1 | | | 7.8 | | 6.9 | | 2.0 | | 2.8 |
| n | 2 | 4 | 2 | 4 | 2 | 4 | 2 | 4 | 2 |

Example 15

Stability of Fungal Alpha-Glucosidases in Ruminal Fluid and Interaction with Pancreatin in Release of Glucose The pre-incubation mixture contained 50 µg each of the fungal alpha-glucosidases: TG L-2000, Aclglu1, Nfiglu1, TauSec098, and TauSec099 (Table 1) dissolved in 2.5 µL and 240 µL cell-free ruminal fluid mixed in wells of a 24 well plate. For control no alpha-glucosidases was added. The mixtures were incubated at 40° C. for 4 h. At the end of the incubation, 250 µL corn starch slurry (10% w/v, Sigma S4126) dissolved in 0.1 M Mes, 5 mM CaCl2 (pH 6) and 2.5 µL pancreatin (Sigma P7545 in 0.1% NaCl, 2.5%, w/v) were added and reaction carried out at 40° C. for 30 min (n=4). The obtained supernatant after centrifugation was diluted 10 times and released glucose was quantified as described in Example 13 using the glucose assay kit from Megazyme.

FIG. 10 shows that a pre-incubation of the five alpha-glucosidases in ruminal fluid at 40° C. for 4 h caused no loss of activity compared with "no pre-incubation" treatment. It appears that more glucose was released in pre-incubated samples than was released in samples that were not pre-incubated (FIG. 10). This might be an indication that these alpha-glucosidase were interacting with starch hydrolases present in the ruminal fluid that had residual level of starch substrate.

Example 16

Synergy of Five Alpha-Glucosidases with Pancreatin in the Release of Glucose from Corn Starch at pH6.0

The reaction mixture contained 0.5 mL corn starch (Sigma S4126) slurry (10% w/v) in 0.1 M Mes (pH6.0) containing 5 mM CaCl2), 50 µg alpha-glucosidase in 2.5 µL and 0 or 2.5 µL pancreatin solution (Sigma P7545, 2.5% w/v in 0.1% NaCl). For control alpha-glucosidase was omitted. The reaction was carried out 40° C. for 60 min (n=4) and released glucose was quantified using the glucose assay kit described in Example 13.

FIG. 11 shows that there was limited production of glucose (0.67 mg/mL reaction mixture) for the control using only pancreatin and no additional enzyme. When alpha-glucosidase only was used, the glucose release was low except for TG L-2000 which showed glucose release (0.80 mg/mL reaction mixture). When both alpha-glucosidase and pancreatin were used together, glucose release increased in the range of 11-20-fold depending on the amount of alpha-glucosidase used. This illustrates the synergistic effect in glucose release from corn starch that can be obtained when any of the five alpha-glucosidases and pancreatin are used.

Example 17

Activity of the Alpha-Glucosidases Treated with Pepsin at pH2.5 and pH6.0

The reaction mixture contained 50 µg of the five alpha-glucosidases of TG L-2000, Aclglu1, Nfiglu1, TauSec098, and TauSec099 (Table 1) in 2.5 µL, 75 µL pepsin (Sigma P7000, stock solution 5000 U/mL) and 1.5 mL maltose (21.5 mg/mL) in 0.1 M Glycine-HCl having 5 mM $CaCl_2$) pH 2.5 or in 0.1 M Mes-NaOH having 5 mM $CaCl_2$ pH6.0. The reaction was carried out at 40° C. for 30 min. At the end of the reaction, the reaction mixture was then diluted 10 times and assayed for glucose release using the glucose assay kit from Megazyme as described in Example 13 above.

TABLE 8

The ratio of activity at pH 2.5 to pH 6.0 for five alpha-glucosidases. The activity at pH 6.0 is regarded as 100%.

| Glucosidases | Activity at pH 2.5 relative to pH 6.0 (%) |
|---|---|
| TG L-2000 | 138 |
| Aclglu1 | 107 |
| Nfiglu1 | 84 |
| TauSec098 | 120 |
| TauSec099 | 167 |

Table 8 shows that all the four glucosidases were more active at pH2.5 than at pH6.0 in the presence of pepsin except for Nfiglu1 which had 84% activity at pH 2.5 compared to pH6.0. Thus, these enzymes show usefulness as feed enzymes for ruminants since they were stable and retained activity in ruminal fluid at 40° C. for 4 h.

Example 18

Use of Glucoamylases in Combination with Metallopeptidases P14L and P7L to Increase Dry Matter Digestion and Gas Production in the Ruminal Fermentation on Corn The effects of the 4 glucoamylases (CS4, TrGA, AfuGA, FvGA) and two metallopeptidases/proteases (P14L, P7L) and their combinations on dry matter digestion (DMD) and gas production at 0, 3, 7, 9, 12, and 24 h incubation/fermentation were evaluated as described below. Both glucoamylases and proteases were applied at 0.25 mg/g concentration.

The effects of the 4 glucoamylases (CS4, TrGA, AfuGA, FvGA) and two metallopeptidases/proteases (P14L, P7L) and their combinations were evaluated on rumen microbial fermentation using dent corn as substrate in in vitro batch culture of rumen fluid. The experiments were based on the protocol established and published earlier (Adesogan, A. T., Krueger, N. A., and Kim, S. C. 2005. Anim. Feed Sci. Technol. 123:211-223). The dent corn used in this in vitro batch fermentation system had 88.8% dry matter (DM), 9.3% crude protein (CP), 3.2% acid detergent fiber (ADF), 8.3% neutral detergent fiber treated with amylase (aNDF), 76.9% non-fibrous carbohydrates (NFC), 88.0% total digestible nutrients (TDN). It was ground to 4 mm. All the enzymes were applied at 0.25 mg enzyme protein per gram dent corn in three separate runs with 4 replications per treatment and the fermentation or incubation lasted 0, 3, 7, 9, 12, and 24 h at 39° C. The ground dent corn was weighed in 6 replications per run into the F57 filter bags (ANKOM Technology, Macedon, NY). Prior to placement in the bottles, the enzymes were diluted in 0.1 M citrate-phosphate buffer (pH 6.0) and added to 0.5 g of the ground dent corn in F57 bags (Krueger, N. A., and A. T. Adesogan. 2008. Anim. Feed Sci. Tech. 145:84-94; Goering, H. K. and P. J. Van Soest. 1970. Agric. Handbook No. 379. ARS USDA, Washington, DC, pp. 20). The F57 filter bags were sealed with an Uline Tabletop Poly Bag Sealer (Impulse® type AIE-200) then immediately placed in the fermentation vessels which were 160 mL serum bottles. Blank bottles consisting of only a filter bag, as well as controls containing only ground dent corn with no enzyme were also included. Ruminal fluid was representatively aspirated from three lactating, ruminally-cannulated Holstein dairy cows 2 to 3 h after consuming total mixed ration (TMR). The TMR ingredient composition fed to the fistulated dairy cows based on dry matter consisted of 38.2% corn silage, 27.3% ground shelled corn, 14.5% soybean meal with 44% crude protein, 9.1% Citrus pulp, 4.5% Feedlot premix, 4.0% alfalfa hay mid bloom, 1.8% energy booster (MS Specialty Nutrition, Dundee, IL), 0.5% Novasil (BASF, Germany), 100% in total.

Rumen fluid collected was filtered through four layers of cheesecloth prior to mixing with pre-warmed artificial saliva (39° C.). The composition of artificial saliva included a micromineral solution of $CaCl_2 \cdot 2H_2O$, $MnCl_2 \cdot 4H_2O$, $CoCl_2 \cdot 6H_2O$, $FeCl_2 \cdot 6H_2O$; a macromineral solution of $Na_2HPO_4 \cdot 12H_2O$, $KH_2PO_4$, $MgSO_4 \cdot 7H_2O$; a buffer solution of $(NH_4)_2HCO_3$ and $NaHCO_3$; a trypticase peptone solution (tryptone, Sigma-Aldrich, St Louise, MO, USA); oxidation-reduction indicator resazurin and a reducing solution containing cysteine HCl, 1 M NaOH, $Na_2S \cdot 9H_2O$ and distilled water. The volume ratio between the rumen fluid and the artificial saliva is 1:2. Buffered rumen fluid (52 mL) was added to 160 mL serum bottles containing the filter bags and the bottles were closed with rubber stoppers and sealed with aluminum seals. The bottles were incubated for 0, 3, 7, 9, 12, and 24 h at 39° C. in a forced-air incubator. At the end of incubation, the filter bags containing the residues were oven dried at 60° C. for 48 h and weighed in order to quantify DMD. The gas pressure within the bottles was measured with a pressure transducer and posteriorly converted to gas volume at 0, 3, 7, 9, 12 and 24 h incubation. The following formula was used for the conversion of gas pressure to gas volume:

$$\text{Gas volume (mL)} = (\text{Gas pressure (psi)} * 4.8843) + 3.1296$$

The equation was formulated based on the experiment conditions using 160 mL serum bottles and is used for all the experiments for Table 9.1-9.2.

Statistical analysis: For all the experiments in Example 18, the data collected were analyzed using the GLIMMIX procedure of SAS (version 9.1; SAS Institute, Cary, NC). Experiments were designed as completely randomized block design where each run was considered a block. Dose was used as fixed effect in the model when enzymes were tested at different doses. Response variable included in-vitro DMD and gas production. Run was considered a random factor. Fixed effects of the model included sampling time for the fermentation parameters measured at different hours post-incubation. The UNIVARIATE procedure of SAS was used to test the residuals for outliers and normality before the final analyses were performed. Treatment effects were declared significant at $P<0.05$ while any trends were defined at $0.05 \le P \le 0.10$.

The results from the evaluation of the four glucoamylases (CS4, TrGA, AfuGA, FvGA) and two metallopeptidases/protease (P14L, P7L) and their combinations on dry matter digestion (DMD) and gas production at 0, 3, 7, 9, 12, and 24 h incubation/fermentation can be found in Tables 9.1.1 to 9.1.4. Both glucoamylases and proteases were applied at 0.25 mg/g concentration.

CS4+/−P14L treatment: No clear effects were observed on DMD in response to CS4 supplementation at 0, 3, and 7 h of incubation or fermentation (Table 9.1.1). However, DMD was improved by 56, 36 and 25% at 9, 12, and 24 h incubation, respectively ($P<0.05$). Similarly, the protease P14L improved DMD by 79, 59, and 32% at 9, 12, and 24 h incubation, respectively ($P<0.05$). Combination of CS4 and P14L improved DMD by 109, 86, and 45% at 9, 12, and 24 h incubation, respectively ($P<0.05$).

TrGA+/−P14L treatment: DMD was increased by 62% and 79% with TrGA and P14L at 9 h incubation, respectively (Table 9.1.2). The combination of both enzymes at 9 h incubation increased DMD to 124% compared to the control ($P<0.01$).

AfuGA+/−P14L treatment: The effects of combining AfuGA and P14L on rumen fermentation parameters are presented in Table 9.1.3. DMD was increased at 7, 9, 12, and 24 h incubation with AfuGA, P14L, and the combination ($P<0.05$). The effects both enzymes in combination are evident as it increased DMD by 119, 146, 108, and 60% at 7, 9, 12, and 24 h incubation, respectively, and the magnitude of effects were greater than the enzymes provided alone ($P<0.05$).

FvGA+/−P14L treatment: The effects of combining FvGA and P14L on rumen fermentation parameters are presented in Table 9.1.4. No effects were observed on DMD in response to FvGA supplementation at 0, 3, and 7 h of incubation; however, DMD was improved by 42, 79 and 93% at 9 h incubation ($P<0.01$) with FvGA, P14L, and their combination, respectively.

All four glucoamylases, the metallopeptidase P14L and their combinations were found to increase fermentation gas production significantly at least at 12 and 24 h incubation ($P<0.05$) (Table 9.1.1-9.14).

CS4, TrGA, AfuGA, FvGA+/−P7L treatment: The effects of combining the 4 glucoamylases (CS4, TrGA, AfuGA, FvGA) with the metallopeptidase/protease P7L on DMD at 0, 3, 7, 9, 12, and 24 h incubation/fermentation are presented in Tables 9.2.1-9.2.4. As with Tables 9.1.1-9.1.4, both glucoamylases and protease were applied at 0.25 mg/g concentration.

Based on the results observed, synergistic or additional effects of the 4 glucoamylases in combination with P7L are observed, irrespective of the incubation time. Additional effects with the combination of CS4 and P7L improved DMD by 49, 112, 72, 60, 55, and 19% at 0, 3, 7, 9, 12, and 24 h incubation, respectively (Table 9.2.1; $P<0.01$). DMD was also increased by 41, 109, 73, 64, 60, and 25% at 0, 3, 7, 9, 12, and 24 h, respectively with the combination of TrGA and P7L (Table 9.2.2; $P<0.01$).

The combination of AfuGA (Table 9.2.3) and P7L improved DMD by 23, 116, 85, 66, 58, and 21% at 0, 3, 7, 9, 12, and 24 h, respectively ($P<0.01$). While the efficacy of FvGA in combination with P7L was effective in improving DMD at 3, 7, 9, and 12 h incubation, no effects are observed at 0, and 24 h when compared with Control (Table 9.2.4). Improved DMD was further supported by greater cumulative gas volume observed at most of the time points of incubation for all the 4 glucoamylases, the protease P7L and their combinations ($P<0.05$) (Table 9.2.1-9.2.4).

TABLE 9.1

1. Effects of CS4 and protease (P14L) and their combination on in vitro dry matter digestibility and gas production.

| Time, h | Control | CS4 | P14L | Combination | SE | P-value |
|---|---|---|---|---|---|---|
| | | Dry matter digestibility, % | | | | |
| 0 | 7.2 | 8.64 | 9.97 | 9.5 | 2.16 | 0.81 |
| 3 | 11.95 | 15.7 | 22.21 | 23.49 | 4.42 | 0.28 |
| 7 | 13.48 | 18.46 | 19.35 | 24.16 | 2.76 | 0.13 |
| 9 | $16.07^c$ | $25.15^b$ | $28.81^{ab}$ | $33.71^a$ | 1.60 | <0.01 |
| 12 | $23.63^b$ | $32.27^{ab}$ | $37.47^{ab}$ | $44.04^a$ | 4.32 | 0.05 |
| 24 | $42^b$ | $52.59^{ab}$ | $55.49^a$ | $61.04^a$ | 4.04 | 0.05 |
| | | Gas volume, mL | | | | |
| 0 | 2.79 | 3.0 | 2.84 | 2.95 | 0.59 | 0.99 |
| 3 | 9.72 | 9.92 | 10.81 | 10.69 | 0.63 | 0.55 |
| 7 | 19.5 | 19.69 | 21.82 | 22.85 | 1.67 | 0.45 |
| 9 | 30.75 | 33.69 | 32.04 | 38.93 | 2.42 | 0.16 |
| 12 | $47.87^b$ | $53.87^{ab}$ | $50.29^b$ | $62.54^a$ | 3.13 | 0.04 |
| 24 | $75.49^c$ | $91.12^{ab}$ | $79.4^{bc}$ | $99.7^a$ | 4.69 | 0.02 |

$^{a\text{-}c}$Means within a row with different superscripts differ (P < 0.05).

TABLE 9.1

2. Effects of TrGA and protease (P14L) and their combination on in vitro dry matter digestibility and gas production.

| Time, h | Control | TrGA | P14L | Combination | SE | P-value |
|---|---|---|---|---|---|---|
| | | Dry matter digestibility, % | | | | |
| 0 | 7.2 | 8.23 | 9.97 | 10.22 | 1.71 | 0.57 |
| 3 | 11.95 | 16.65 | 22.20 | 25.81 | 8.02 | 0.17 |
| 7 | 13.48 | 20.65 | 19.35 | 26.11 | 3.28 | 0.13 |
| 9 | $16.07^c$ | $26.11^b$ | $28.81^b$ | $36.01^a$ | 1.54 | <0.01 |
| 12 | $23.62^b$ | $34.11^{ab}$ | $37.47^a$ | $44.05^a$ | 4.14 | 0.05 |
| 24 | $42^b$ | $56.75^a$ | $55.49^{ab}$ | $63.63^a$ | 4.17 | 0.04 |
| | | Gas volume, mL | | | | |
| 0 | 2.79 | 3.09 | 2.84 | 3.01 | 0.51 | 0.97 |
| 3 | 9.72 | 10.08 | 10.82 | 12.31 | 0.87 | 0.23 |
| 7 | 19.5 | 20.7 | 21.82 | 23.56 | 1.98 | 0.54 |
| 9 | 30.75 | 35.57 | 32.05 | 41.69 | 2.70 | 0.08 |
| 12 | $47.87^b$ | $56.28^{ab}$ | $20.29^b$ | $65.99^a$ | 3.42 | 0.02 |
| 24 | $75.49^b$ | $97.24^a$ | $79.41^b$ | $106.26^a$ | 5.09 | <0.01 |

$^{a\text{-}c}$Means within a row with different superscripts differ (P < 0.05).

TABLE 9.1

3. Effects of AfuGA and protease (P14L) and their combination
on in vitro dry matter digestibility and gas production.

| Time, h | Control | AfuGA | P14L | Combination | SE | P-value |
|---|---|---|---|---|---|---|
| | | | Dry matter digestibility, % | | | |
| 0 | 7.2 | 10.19 | 9.97 | 11.94 | 2.02 | 0.46 |
| 3 | 11.95 | 18.48 | 22.20 | 26.42 | 4.65 | 0.23 |
| 7 | 13.48 [b] | 23.26 [ab] | 19.35 [ab] | 29.57 [a] | 3.17 | 0.04 |
| 9 | 16.07 [c] | 30.73 [b] | 28.81 [b] | 39.58 [a] | 1.56 | <0.01 |
| 12 | 23.62 [b] | 37.18 [ab] | 37.47 [ab] | 49.07 [a] | 5.04 | 0.04 |
| 24 | 42 [b] | 57.59 [a] | 55.48 [a] | 67.27 [a] | 3.64 | <0.01 |
| | | | Gas volume, mL | | | |
| 0 | 2.78 | 2.83 | 2.84 | 2.96 | 0.50 | 0.99 |
| 3 | 9.72 | 10.47 | 10.83 | 13.19 | 0.80 | 0.07 |
| 7 | 19.5 | 21.12 | 21.83 | 28.76 | 1.52 | 0.01 |
| 9 | 30.74 [b] | 37.62 [b] | 32.06 [b] | 48.37 [a] | 2.40 | <0.01 |
| 12 | 47.87 [c] | 59.98 [b] | 50.30 [c] | 75.11 [a] | 2.60 | <0.01 |
| 24 | 75.49 [c] | 102.68 [b] | 79.45 [c] | 121.87 [a] | 3.37 | <0.01 |

[a-c] Means within a row with different superscripts differ (P < 0.05).

TABLE 9.1

4. Effects of FvGA and protease (P14L) and their combination
on in vitro dry matter digestibility and gas production.

| Time, h | Control | FvGA | P14L | Combination | SE | P-value |
|---|---|---|---|---|---|---|
| | | | Dry matter digestibility, % | | | |
| 0 | 7.2 | 7.09 | 9.97 | 9.10 | 2.54 | 0.81 |
| 3 | 11.95 | 15.17 | 22.22 | 24.28 | 4.13 | 0.20 |
| 7 | 13.48 | 16.47 | 19.35 | 21.36 | 2.55 | 0.22 |
| 9 | 16.07[c] | 22.74[b] | 28.81[ab] | 31.01[a] | 1.99 | <0.01 |
| 12 | 23.63 | 29.42 | 37.47 | 37.42 | 5.0 | 0.17 |
| 24 | 42 | 44.89 | 55.49 | 56.47 | 3.74 | 0.06 |
| | | | Gas volume, mL | | | |
| 0 | 2.79 | 2.99 | 2.84 | 3.03 | 0.46 | 0.98 |
| 3 | 9.72 | 10.54 | 10.82 | 11.93 | 0.64 | 0.19 |
| 7 | 19.5[b] | 21.77[ab] | 21.82[ab] | 25.42[a] | 1.22 | 0.05 |
| 9 | 30.75[b] | 35.77[ab] | 32.05[b] | 41.47[a] | 2.09 | 0.03 |
| 12 | 47.87[b] | 54.39[b] | 50.30[b] | 62.26[a] | 2.21 | <0.01 |
| 24 | 75.49[b] | 85.68[b] | 79.45[b] | 96.57[a] | 3.19 | <0.01 |

[a-c]Means within a row with different superscripts differ (P < 0.05).

TABLE 9.2

1 Effects of CS4 and protease (P7L) and their combination
on in vitro dry matter digestibility and gas production.

| Time, h | Control | CS4 | P7L | Combination | SE | P-value |
|---|---|---|---|---|---|---|
| | | | Dry matter digestibility, % | | | |
| 0 | 9.21 [b] | 10.8 [a] | 12.6 [a] | 13.7 [a] | 0.77 | <0.01 |
| 3 | 14.7 [d] | 17.8 [c] | 24.2 [b] | 31.1 [a] | 1.01 | <0.01 |
| 7 | 25.0 [c] | 29.7 [b] | 40.2 [a] | 43.1 [a] | 1.43 | <0.01 |
| 9 | 30.3 [d] | 36.0 [c] | 44.7 [b] | 48.5 [a] | 1.37 | <0.01 |
| 12 | 31.9 [c] | 40.2 [b] | 43.8 [b] | 49.5 [a] | 1.86 | <0.01 |
| 24 | 52.5 [b] | 56.8 [b] | 57.7 [ab] | 62.4 [a] | 1.83 | <0.01 |
| | | | Gas volume, mL | | | |
| 0 | 2.98 | 3.64 | 3.24 | 3.39 | 0.23 | 0.23 |
| 3 | 6.50 [b] | 6.45 [b] | 8.84 [a] | 9.11 [a] | 0.54 | <0.01 |
| 7 | 11.27 [d] | 13.31 [c] | 14.50 [b] | 17.19 [a] | 0.34 | <0.01 |
| 9 | 14.46 [c] | 20.82 [b] | 19.67 [b] | 24.35 [a] | 0.98 | <0.01 |
| 12 | 13.59 [c] | 20.12 [b] | 21.02 [b] | 24.35 [a] | 0.52 | <0.01 |
| 24 | 31.88 [b] | 40.45 [a] | 31.42 [b] | 43.34 [a] | 1.25 | <0.01 |

[a-c] Means within a row with different superscripts differ (P < 0.05).

TABLE 9.2

2. Effects of TrGA and protease (P7L) and their combination
on in vitro dry matter digestibility and gas production.

| Time, h | Control | TrGA | P7L | Combination | SE | P-value |
|---|---|---|---|---|---|---|
| | | | Dry matter digestibility, % | | | |
| 0 | 9.21 [c] | 10.8 [b] | 11.1 [b] | 13.0 [a] | 0.45 | <0.01 |
| 3 | 14.7 [d] | 18.0 [c] | 24.2 [b] | 30.7 [a] | 1.04 | <0.01 |
| 7 | 25.0 [c] | 28.9 [b] | 40.2 [a] | 43.3 [a] | 1.33 | <0.01 |
| 9 | 30.3 [c] | 36.5 [c] | 44.7 [b] | 49.6 [a] | 1.06 | <0.01 |
| 12 | 31.9 [c] | 41.0 [b] | 43.8 [b] | 51.1 [a] | 1.66 | <0.01 |
| 24 | 52.5 [c] | 58.8 [b] | 57.7 [b] | 65.5 [a] | 1.76 | <0.01 |
| | | | Gas volume, mL | | | |
| 0 | 2.98 | 3.53 | 3.24 | 3.53 | 0.22 | 0.24 |
| 3 | 6.50 [b] | 6.82 [b] | 8.83 [a] | 10.15 [a] | 0.47 | <0.01 |
| 7 | 11.27 [d] | 13.03 [c] | 14.26 [b] | 18.26 [a] | 0.47 | <0.01 |
| 9 | 14.46 [c] | 22.03 [ab] | 19.67 [b] | 23.43 [a] | 1.13 | <0.01 |

TABLE 9.2-continued

2. Effects of TrGA and protease (P7L) and their combination
on in vitro dry matter digestibility and gas production.

| Time, h | Control | TrGA | P7L | Combination | SE | P-value |
|---------|---------|------|-----|-------------|-----|---------|
| 12 | 13.59 [c] | 20.33 [b] | 21.02 [b] | 26.34 [a] | 0.60 | <0.01 |
| 24 | 31.88 [c] | 41.60 [b] | 31.42 [c] | 45.16 [a] | 1.45 | <0.01 |

[a-c] Means within a row with different superscripts differ (P < 0.05).

TABLE 9.2

3. Effects of AfuGA and protease (P7L) and their combination
on in vitro dry matter digestibility and gas production.

| Time, h | Control | AfuGA | P7L | Combination | SE | P-value |
|---------|---------|-------|-----|-------------|-----|---------|
| | | Dry matter digestibility, % | | | | |
| 0 | 9.21 [b] | 12.1 [a] | 11.1 [a] | 11.3 [a] | 0.55 | <0.01 |
| 3 | 14.7 [d] | 20.1 [c] | 24.2 [b] | 31.7 [a] | 0.92 | <0.01 |
| 7 | 25.0 [d] | 33.5 [c] | 40.2 [b] | 46.2 [a] | 1.45 | <0.01 |
| 9 | 30.2 [d] | 38.5 [c] | 44.7 [b] | 50.2 [a] | 1.00 | <0.01 |
| 12 | 31.9 [c] | 42.0 [b] | 43.8 [b] | 50.3 [a] | 1.81 | <0.01 |
| 24 | 52.5 [c] | 60.4 [ab] | 57.7 [bc] | 63.6 [a] | 1.90 | <0.01 |
| | | Gas volume, mL | | | | |
| 0 | 2.98 | 3.85 | 3.24 | 3.24 | 0.25 | 0.12 |
| 3 | 6.50 [c] | 8.35 [b] | 8.84 [b] | 10.88 [a] | 0.53 | <0.01 |
| 7 | 11.27 [c] | 15.05 [b] | 14.50 [b] | 17.44 [a] | 0.35 | <0.01 |
| 9 | 14.46 [b] | 21.94 [a] | 19.67 [a] | 21.86 [a] | 1.18 | 0.02 |
| 12 | 13.59 [c] | 22.55 [b] | 21.02 [b] | 25.17 [a] | 0.65 | <0.01 |
| 24 | 31.88 [b] | 44.24 [a] | 31.42 [b] | 43.19 [a] | 1.29 | <0.01 |

[a-c] Means within a row with different superscripts differ (P < 0.05).

TABLE 9.2

4. Effects of FvGA and protease (P7L) and their combination
on in vitro dry matter digestibility and gas production.

| Time, h | Control | FvGA | P7L | Combination | SE | P-value |
|---------|---------|------|-----|-------------|-----|---------|
| | | Dry matter digestibility, % | | | | |
| 0 | 9.20 | 9.85 | 11.1 | 10.7 | 0.51 | 0.05 |
| 3 | 14.7 [c] | 18.0 [b] | 24.2 [a] | 25.3 [a] | 1.09 | <0.01 |
| 7 | 25.1 [b] | 28.6 [b] | 40.2 [a] | 40.2 [a] | 1.48 | <0.01 |
| 9 | 30.3 [c] | 33.7 [b] | 44.7 [b] | 45.9 [b] | 1.10 | <0.01 |
| 12 | 31.9 [b] | 34.9 [b] | 43.8 [a] | 46.9 [a] | 1.99 | <0.01 |
| 24 | 52.5 [ab] | 50.2 [b] | 57.7 [a] | 56.8 [a] | 1.93 | 0.03 |
| | | Gas volume, mL | | | | |
| 0 | 2.98 | 3.64 | 3.24 | 3.8 | 0.35 | 0.35 |
| 3 | 6.50 [c] | 8.34 [b] | 8.84 [ab] | 10.08 [a] | 0.49 | <0.01 |
| 7 | 11.27 [c] | 13.46 [b] | 14.50 [b] | 15.91 [a] | 0.39 | <0.01 |
| 9 | 14.46 [b] | 18.06 [a] | 19.67 [a] | 19.73 [a] | 0.94 | 0.16 |
| 12 | 13.59 [c] | 19.23 [b] | 21.02 [a] | 22.45 [a] | 0.60 | <0.01 |
| 24 | 31.88 [b] | 33.94 [ab] | 31.42 [b] | 36.40 [a] | 1.31 | 0.041 |

[a-c] Means within a row with different superscripts differ (P < 0.05).

Example 19

Maltose Hydrolysis by Glucoamylases

Typically, it is glucose that is absorbed in animals. Maltose is a disaccharide formed from two units of glucose. Thus, maltose needs to be hydrolyzed to glucose monomers in order to be absorbed. It is advantageous for a glucoamylase to have high catalytic activity on the substrate maltose in addition to other preferred properties for use as a feed additive enzyme. Preferably a glucoamylase should have at least 20% of the activity on the substrate maltose when compared to the activity of TrGA under the test conditions described herein.

Glucoamylase activity on maltose was determined as follows. A reaction mixture was prepared that contained 2% (w/v) or 8% (w/v) maltose (M-5885, Sigma), and 10 μg glucoamylase in 50 mM Mes-NaOH (pH6.0) containing 5 mM $CaCl_2$), in a final volume of 0.05 mL in a 96 well microplate. Each glucoamylase-maltose reaction was repeated in triplicate.

The reaction was carried at 40° C. for 20 min, which was in the linear range with respect to glucose release. The reaction was run in a PCR machine at 95° C. for 5 min. After cooling to room temperature (23° C.), 10 μL of the reaction mixture which was diluted to a concentration in the range of 0.5 to 0.9 mg glucose per mL was mixed with 0.24 mL GOPOD reagent (D-Glucose Assay Kit, GOPOD Format from Megazyme) in a microplate. The mixture was then incubated at 50° C. for 20 min and absorbance at 510 nm was read. Glucose standard from the manufacturer was used to create a standard curve for calibration.

The data in Table 10 shows that all the glucoamylases tested had activity on maltose at conditions similar or close to those found in in vivo digestive conditions, such as nearly neutral pH of 6.0.

It was observed that AnGA was an exception in that it on the substrate maltose under these test conditions. Thus, AnGA is not a suitable glucoamylase for use as described herein.

TABLE 10

| | Maltose hydrolysis by four glucoamylases at two maltose concentrations and pH 6.0. | |
| --- | --- | --- |
| Treatment | Maltose 2% (w/v) | Maltose 8% (w/v) |
| TrGA* | 100 | 100 |
| CS4 | 44 | 44 |
| AfuGA | 41 | 33 |
| AnGA | 15 | 12 |
| Control (minus enzyme) | 0.2 | 2 |

*Activity of TrGA on maltose was treated as 100%.

What is claimed is:

1. A method for increasing starch digestibility and glucose yield in a ruminant which comprises:

(a) adding at least one fungal glucoamylase as a feed additive to feed for a ruminant, wherein the at least one fungal glucoamylase is an EC 3.2.1.3 enzyme derived from *Trichoderma reesei* and:

(i) has at least 20% activity at pH less than or equal to 3 in the presence of pepsin as compared to activity of the hydrolase at pH 6 in the presence of pepsin;

(ii) is active in at least two of the three digestive chambers of a ruminant comprising a rumen, an abomasum, and a small intestine;

(iii) works with digestive enzymes present in the digestive chambers of the ruminant to increase starch digestibility and glucose yield; and (iv) has at least 20% catalytic activity on maltose; and (b) administering said feed additive to the ruminant, wherein starch digestibility and glucose yield in the ruminant is increased by said addition.

2. The method of claim 1 wherein the at least one glucoamylase enzyme is capable of hydrolyzing raw starch under conditions comparable to those found in the rumen or abomasum.

3. The method of claim 1, further comprising adding at least one EC 3.2.1.1 alpha-amylase to the feed.

4. The method of claim 3, further comprising adding at least one xylanase to the feed.

5. The method of claim 1, further comprising adding at least one protease to the feed.

6. The method of claim 5 wherein the protease is selected from the group consisting of an acid protease and a neutral metalloprotease.

7. The method of claim 6 wherein the protease is a fungal aspartic protease or a bacterial neutral metalloprotease.

8. The method of claim 5, further comprising adding at least one xylanase to the feed.

9. The method of claim 1, further comprising adding at least one xylanase to the feed.

\* \* \* \* \*